United States Patent
Van Der Vuurst De Vries et al.

(10) Patent No.: US 7,186,818 B2
(45) Date of Patent: Mar. 6, 2007

(54) DNA ENCODING SOLUBLE VARIANTS OF HUMAN OX2 RECEPTORS

(75) Inventors: Anne-Renee Van Der Vuurst De Vries, Seattle, WA (US); Laurent J. Galibert, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 179 days.

(21) Appl. No.: 10/475,691

(22) PCT Filed: Apr. 25, 2002

(86) PCT No.: PCT/US02/13087

§ 371 (c)(1), (2), (4) Date: May 14, 2004

(87) PCT Pub. No.: WO02/088164

PCT Pub. Date: Nov. 7, 2002

(65) Prior Publication Data

US 2004/0214187 A1 Oct. 28, 2004

Related U.S. Application Data

(60) Provisional application No. 60/286,686, filed on Apr. 26, 2001.

(51) Int. Cl.
*C07H 21/04* (2006.01)
*C12N 15/00* (2006.01)
*C12N 5/10* (2006.01)
*C12P 21/06* (2006.01)
*A61K 31/713* (2006.01)

(52) U.S. Cl. ............... 536/23.5; 435/320.1; 435/252.3; 435/455; 435/69.1; 514/44

(58) Field of Classification Search ............... None
See application file for complete search history.

(56) References Cited

U.S. PATENT DOCUMENTS 6,476,195 B1 * 11/2002 Komatsoulis et al. ....... 530/350
2004/0126777 A1 * 7/2004 Bhatt et al. .................... 435/6

FOREIGN PATENT DOCUMENTS

WO    WO 00/70045 A1    11/2000

OTHER PUBLICATIONS

Ehrstrom et al., 2005, J. Clin. Endocrinol. Metab., 90: 2370-2377.*

* cited by examiner

*Primary Examiner*—Phillip Gambel
*Assistant Examiner*—Ilia Ouspenski
(74) *Attorney, Agent, or Firm*—Patricia Anne Perkins

(57) ABSTRACT

Isolated receptors, nucleic acids encoding such receptors, and pharmaceutical compositions made therefrom, are disclosed. The isolated receptors can be used to regulate an immune response. The receptors are also useful in screening for inhibitors or agonists thereof.

8 Claims, 3 Drawing Sheets

```
Leader
hOX2R    MLCPWRTANLGLLLILTIFLVAEA
mOX2R    MFCFWRTSALAVLLIWGVFVAGS
rOX2R    MLCFWRTSHVAVLLIWGVFAAES V-domain                                           .....A......        ....B...                       ..C..                       ..C'..
hOX2R    EGAAQPNNSLMLQTSKENHALASSSLCMDEKQITQN-YSKVLAEVNTSWPVKMATNAVLCCPPIALRNLIITWEILLRGQPSCTKAYRKET
mOX2R                                              SCTDKNQTTQNNSSSPLTQVNTTVSVQIGTKALLQCFSIPLTKAVLITWIIKLRGLPSCTIAYKVDT
rOX2R                                              SCPDKNQTMQNNSST-MTEVNTTVFVQMGKKALLCCPSISLTKVLIITWTITLRGQPSCIISYKADT ..C''...  ...D...                     .....E...   ....F.....                ....G....
hOX2R    NETKETNCTDERITWVSRPDQNSDLQIRPVAITHDGYYRCIMVTPDGNFHRGYHLQVLVTP
mOX2R    K-TNETSCLGRNITWASTPDHSPELQISAVTLQHEGTYTCETVTPEGNFEKNYDLQVLVPP
rOX2R    RETHESNCSDRSITWASTPDLAPDLQISAVALQHEGRYSCDIAVPDGNFQNIYDLQVLVPP C-domain..A..    ....B....                      ....C....   ....C'..  ....E.....  ...F......
hOX2R    EVTLFQNRNRTAVCKAVAGKPAAQISWIPEGDCATKQEYWSNGTVTVKSTCHWEVHNVSTVTCHVSH
mOX2R    EVTYFPEKNRSAVCEAMAGKPAAQISWSPDGDCVTTSESHSNGTVTVRSTCHWEQNNVSDVSCIVSH
rOX2R    EVTHFPGENRTAVCEAIAGKPAAQISWTPDGDCVAKNESHSNGTVTVRSTCHWEQSHVSVVFCVVSH ...G...                                        Transmembrane
hOX2R    LTG-NKSLYIELLPVPGAKKSAK                        LYIPYILLTIILTIVGFIWLL
mOX2R    LTG-NQSLSIELS--RGGNQSLR                        PYIPYIIPSIIILIIGCICLL
rOX2R    LTTGNQSLSIELG--RGGDQLLG                        SYIQYIIPSIIILIIGCICLL Cytoplasmic
hOX2R    KVNGCRKYKLNKTESTPVVEEDEMQPYASYTEKNNPLYDTTNKVKASQALQSEVD-TDLHTL
mOX2R    KISGFRKCKLPKLEATSALEEDEMQPYASYTEKSNPLYDTVTKVEAFPVSQGEVNGTDCLTLSAIGI
rOX2R    KISGCRKCKLPKSGATPDIEEDEMQPYASYTEKSNPLYDTVTTEAHPASQGKVNGTDCLTLSAMGI
```

Figure 1

```
             10        20        30        40        50        60        70        80        90       100
S1  MLCPWRTANLGLLLILTIFLVAEAEGAAQPNNSLMLQTSKENHALASSSLCMDEKQITQNYSKVLAEVNTSWPVKMATNAVLCCPPIALRNLIIITWEII
S2  MLCPWRTANLGLLLILTIFLVAEAEGAAQPNNSLMLQTSKENHALASSSLCMDEKQITQNYSKVLAEVNTSWPVKMATNAVLCCPPIALRNLIIITWEII
FL  MLCPWRTANLGLLLILTIFLVAEAEGAAQPNNSLMLQTSKENHALASSSLCMDEKQITQNYSKVLAEVNTSWPVKMATNAVLCCPPIALRNLIIITWEII 110       120       130       140       150       160       170       180       190       200
S1  LRGQPSCTKAYRKETNETKETNCTDERITWVSRPDQNSDLQIRPVAITHDGYYRCIMVTPDGNFHRGYHLQVLVTPEVTLFQNRNRTAVCKAVAGKPAAQ
S2  LRGQPSCTKAYRKETNETKETNCTDERITWVSRPDQNSDLQIRPVAITHDGYYRCIMVTPDGNFHRGYHLQVLVTPEVTLFQNRNRTAVCKAVAGKPAAQ
FL  LRGQPSCTKAYRKETNETKETNCTDERITWVSRPDQNSDLQIRPVAITHDGYYRCIMVTPDGNFHRGYHLQVLVTPEVTLFQNRNRTAVCKAVAGKPAAQ 210       220       230       240       250       260       270       280       290       300
S1  ISWIPEGDCATKQEYWSNGTVTVKSTCHWEVHNVSTVTCHVSHLTGNKSLYIELLPENIN---------------------------------------
S2  ISWIPEGDCATKQEYWSNGTVTVKSTCHWEVHNVSTVTCHVSHLTGNKSLYIELLPG-----------------------------------------
FL  ISWIPEGDCATKQEYWSNGTVTVKSTCHWEVHNVSTVTCHVSHLTGNKSLYIELLPVPGAKKSAKLYIPYIILTIILTIVGFIWLLKVNGCRKYKLNKT 310       320       330       340
S1  ----------------------------------------
S2  ----------------------------------------
FL  ESTPVVEEDEMQPYASYTEKNNPLYDTNKVKASQALQSEVDTDLHTL
```

Figure 2

```
                    10        20        30        40        50        60        70        80        90       100
mOX2R     MFCFWRTSALAVLLIWGVFVAGSSCTDKNQTTQNNSSSPLTQVNTTVSVQIGTKALLCCFSIPLTKAVLITWIIKLRGLPSCTIAYKVDTKTNETSCLGR
variant1  MFCFWRTSALAVLLIWGVFVAGSSCTDKNQTTQNNSSSPLTQVNTTVSVQIGTKALLCCFSIPLTKAVLITWIIKLRGLPSCTIAYKVDTKTNETSCLGR
soluble1  MFCFWRTSALAVLLIWGVFVAGSSCTDKNQTTQNNSSSPLTQV-----------------------------------------------------------
          ******************************************

110       120       130       140       150       160       170       180       190       200
mOX2R     NITWASTPDHSPELQISAVTLQHEGTYTCETVTPEGNFEKNYDLQVLVPPEVTYFPEKNRSAVCEAMAGKPAAQISWSPDGDCVTTSESHSNGTVTVRST
variant1  ------------------------------------------PPEVTYFPEKNRSAVCEAMAGKPAAQISWSPDGDCVTTSESHSNGTVTVRST
soluble1  NITWASTPDHSPELQISAVTLQHEGTYTCETVTPEGNFEKNYDLQVLVPPEVTYFPEKNRSAVCEAMAGKPAAQISWSPDGDCVTTSESHSNGTVTVRST
                                                    ************************************************

210       220       230       240       250       260       270       280       290       300
mOX2R     CHWEQNNVSDVSCIVSHLTGNQSLSIELSRGGNQSLRPYIPYIIPSIILLIIGCICLLKISGFRKCKLPKLEATSAIEEDEMQPYASYTEKSNPLYDTV
variant1  CHWEQNNVSDVSCIVSHLTGNQSLSIELSRGGNQSLRPYIPYIIPSIILLIIGCICLLKISGFRKCKLPKLEATSAIEEDEMQPYASYTEKSNPLYDTV
soluble1  CHWEQNNVSDVSCIVSHLTGNQSLSIELSRGENANCQN----------------------------------------------------------
          *******************************. :

310       320
mOX2R     TKVEAFPVSQGEVNGTDCLTLSAIGI
variant1  TKVEAFPVSQGEVNGTDCLTLSAIGI
soluble1  --------------------------
```

Figure 3

DNA ENCODING SOLUBLE VARIANTS OF HUMAN OX2 RECEPTORS

CROSS REFERENCE TO RELATED APPLICATIONS

This application is a national-stage application under 35 U.S.C. § 371 of international application PCT/US02/13087, filed on Apr. 25, 2002, designating the U.S. and published in English on Nov. 2, 2002, which claims the benefit under 35 U.S.C. § 119 of U.S. Provisional application Ser. No. 60/286,686 filed Apr. 26, 2001; the disclosures of which are incorporated herein by reference.

TECHNICAL FIELD OF THE INVENTION

The present invention relates generally to the field of cytokine receptors, and more specifically to cytokine receptor/ligand pairs having immunoregulatory activity.

BACKGROUND OF THE INVENTION

Efficient functioning of the immune system requires a fine balance between cell proliferation and differentiation and cell death, to ensure that the immune system is capable of reacting to foreign, but not self antigens. Regulation of the immune system occurs by the interaction of numerous receptor/ligand pairs, some of which have been identified and their functions delineated. However, there are molecules that are known to be present on or expressed by cells involved in an immune response, but for which a function (or functions) and/or binding partner is not known.

One such molecule is referred to as OX2; it has been identified on a variety of cells, including B and T lymphocytes, neurons, follicular dendritic cells, endothelial cells and thymocytes (Barclay et al., *Immunol.* 44:727; 1981). OX2 is a transmembrane protein comprising two immunoglobulin (Ig) domains and a short cytoplasmic domain that is thought to be a ligand for a receptor (Clark et al., *EMBO J.* 4:113; 1985). OX2 has been designated the human leukocyte antigen CD200 (*HLDA7: 7th Workshop and Conference on Human Leukocyte Differentiation Antigens*, Harrogate, UK, 20 to 24 Jun. 2000).

A counterstructure for OX2 was identified in rat splenic lysates using a monoclonal antibody, and the cDNA encoding this counterstructure (also referred to as OX2 receptor or OX2R) was isolated (Wright et al., *Immunity* 13:233; 2000). The counterstructure was found to be a transmembrane protein which, like OX2, comprised two Ig domains; the cytoplasmic domain, however, was longer than that of OX2 and included a motif common to other receptors that bind signaling adaptor molecules, including beta integrins (Patil et al., *J. Biol. Chem.* 274:28575; 1999). Human homologs of the rat OX2R were identified by Barclay et al. (WO 00/70045, published Nov. 23, 2000).

The OX2R, unlike OX2/CD200, exhibited limited distribution, with expression limited to cells of the myeloid lineage (Wright et al., supra; Preston et al., *Eur. J. Immunol.* 27:1911, 1997). Moreover, the lack of OX2/CD200 in gene-targeted mice led to enhanced susceptibility to experimental autoimmune encephalomyelitis (EAE) and collagen-induced arthritis (CIA), both of which are models for human autoimmune disease (Hoek et al., *Science* 290:1768; 2000). Taken together, these results imply an important role for OX2R/CD200R in the regulation of myeloid lineage cells, and hence the immune response. Accordingly, there is a need in the art to identify additional forms of human OX2R/CD200R, particularly soluble forms that can be used in therapeutic or diagnostic applications.

SUMMARY OF THE INVENTION

The present invention provides a novel receptor, referred to as human OX2 receptor (OX2R), a Type I transmembrane protein having 348 amino acid residues that interacts with OX2/CD200. Triggering of OX2R by OX2 appears to downregulate or inhibit the activity of macrophages and other myeloid lineage cells. Soluble forms of the receptor can be prepared and used to interfere with signal transduction through membrane-bound OX2R, and hence the inhibition of cells of myeloid lineage. Soluble forms of OX2R can also be used to detect or enumerate cells expressing OX2/CD200, and to deliver selected agents to such cells. Preferred soluble forms of OX2R are disclosed.

Soluble forms of the receptor will also be useful in vitro to screen for agonists or antagonists of OX2R activity utilizing one or more screening methods, which methods also form an aspect of the present invention. In one aspect, the inventive methods utilize homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence. In another aspect, the inventive methods utilize heterogeneous assay formats such as enzyme-linked immunosorbant assays (ELISA) or radioimmunoassays. In yet another aspect of the invention are cell-based assays, for example those utilizing reporter genes, as well as functional assays that analyze the effect of an antagonist or agonist on biological function(s).

The invention further provides methods for producing information comprising the identity of a compound that alters one or more biological activities of OX2R/CD200R, the method comprising using assay methods of the invention to identify one or more compounds that alter the binding of OX2R/CD200R and the counterstructure OX2/CD200. In one preferred embodiment, the compound increases (or agonizes) the binding of OX2R/CD200R and OX2/CD200, and in another distinct embodiment, the compound decreases (or antagonizes) the binding of OX2R/CD200R and OX2/CD200.

Preferably the biological activity of OX2R/CD200R that is increased or upregulated is selected from the group consisting of downregulation of deleterious effects of an immune or inflammatory response (including atherosclerosis, arthritis, multiple sclerosis (MS), systemic lupus erythematosous (SLE), thrombosis, graft versus host disease, and/or graft rejection). In a distinct embodiment, the biological activity of OX2R/CD200R that is increased or upregulated is selected from the group consisting of upregulation of an immune response, prevention or treatment of infectious disease, and prevention or treatment of neoplastic disease.

Also provided by the invention is the information produced according to the inventive methods, said information comprising the identity of a compound that alters the biological activity of OX2R/CD200R, and preferably embodied in a storage medium selected from the group consisting of the brains of living organisms, paper, magnetic tape, optical tape, floppy disks, compact disks, computer system hard drives, and computer memory units. In a further aspect, the invention provides a database comprising said information, wherein the information is preferably embodied in a computer-readable medium, and a separate embodiment wherein the information is embodied in a human-readable medium.

Additionally provided by the invention is a computer system comprising a database containing records pertaining to a plurality of compounds, wherein the records comprise results of an assay of the invention, and a user interface allowing a user to access information regarding the plurality of compounds. In another aspect of the invention, a computer system is provided for storing and retrieving data on a plurality of compounds, the computer system comprising:

(a) input means for entering data for the compounds into a storage medium;

(b) a processor for creating an individual record for each compound, the processor assigning specific identifying values for each compound;

(c) means for selecting one or more of the records based on results in an assay; and (d) means for transmitting information in the record or records to an output device to produce a report; preferably a report in human-readable form, and wherein the computer system preferably further comprises a video display unit.

The invention also provides a method of using the computer system of the invention to select one or more compounds for testing from a plurality of compounds having records stored in a database, the method comprising: displaying a list of said records or a field for entering information identifying one or more of said records; and selecting one or more of the records from the list or the record or records identified by entering information in the field.

Further, the invention provides a method of operating a computer system for analyzing compounds that modulate the interaction of OX2R/CD200R and OX2/CD200, the method comprising:

(a) entering data relating to a plurality of compounds into a storage medium;

(b) processing the data to create an individual record for each compound;

(c) testing compounds for the ability to modulate binding of OX2R/CD200R and OX2/CD200; and (d) communicating results from the testing into the storage medium such that results for each compound are associated with the individual record for that compound; wherein in one embodiment the storage medium comprises one or more computer memory units, and in another embodiment the computer system further comprises a video display unit.

In yet another aspect of the invention, a database is provided comprising records generated according to the methods of the invention, and a method is provided for selecting compounds that modulate the interaction of OX2R/CD200R and OX2/CD200, comprising compiling said database, analyzing the testing results, and selecting one or more compounds.

Candidate molecules that are determined to agonize or antagonize an OX2R/CD200R signaling activity are useful, for example, for the further definition of OX2R/CD200R-mediated signaling pathways, and for the manipulation of OX2R/CD200R-mediated immune and/or neurologic responses. Moreover, OX2R/CD200R signaling agonists and antagonists provide therapeutic agents for treating disorders of the immune system, and inflammatory disorders, as well as treatment of conditions characterized by malignant cells.

The cytoplasmic domain of OX2R will be useful in developing assays for inhibitors of signal transduction, for example, for screening for molecules that inhibit interaction of OX2R with intracellular signaling proteins. Deleted forms and fusion proteins comprising the novel receptor are also disclosed. These and other aspects of the present invention will become evident upon reference to the following detailed description of the invention.

BRIEF DESCRIPTION OF THE DRAWINGS

FIG. 1 represents an alignment of the human, mouse and rat orthologs of OX2R. The extracellular potential N-linked glycosylation sites are highlighted in gray. Conserved cysteines (in V-domain) and tyrosines (in cytoplasmic domain) are underlined; the NPXY site that is believed to be important in binding signaling adaptor molecules is shown in bold face.

FIG. 2 illustrates the similarities and differences between the inventive soluble forms of human OX2R/CD200R (denoted 'S1' and 'S2') and full length OX2R/CD200R (denoted 'FL'). The transmembrane region of the full length form is underlined; the amino acids that differ between the full-length form and the two variants of OX2R/CD200R are shown in bold face. FL corresponds to SEQ ID NO:2; S1 corresponds to SEQ ID NO:4, and S2 corresponds to SEQ ID NO:6.

FIG. 3 compares the varying forms of murine OX2R isolated. The full-length from is denoted 'mOX2R;' 'Variant 1' refers to a variant having a transmembrane domain, but lacking a portion of the extracellular domain. The transmembrane region of the full-length form and the corresponding region of variant 1 are underlined. 'Soluble1' refers to a splice-variant of mOX2R that lacks a transmembrane region; the amino acids that differ between Soluble1 and full-length mOX2R are shown in bold face. mOX2R corresponds to SEQ ID NO:8; Variant1 corresponds to SEQ ID NO:10, and Soluble1 corresponds to SEQ ID NO12.

DETAILED DESCRIPTION OF THE INVENTION

A novel cDNA was identified by subtractive hybridization of cDNAs derived from human dendritic cell (DC) versus cDNAs derived from monocytes (both derived from Flt3-ligand (FL)-treated healthy volunteers); two alternate forms were identified by polymerase chain reaction (PCR). SEQ ID NO:1 shows the nucleotide and amino acid sequence of the full-length protein; the nucleotide and amino acid sequences of the two alternate, soluble forms are shown in SEQ ID NOs:3 and 5.

OX2R/CD200R is a member of the Immunoglobulin Superfamily; it most closely resembles OX2/CD200 in the extracellular region. In the mouse, OX2R is expressed primarily on myeloid cells, although there is some evidence to suggest that it is also expressed on activated T cells (Gorczynski et al., *J. Immunol.* 165:4854, 2000). OX2R and its ligand, CD200, are likely to play an integral role in regulation of the immune and inflammatory response.

DNAs, Proteins and Analogs

The present invention provides isolated OX2R polypeptides and analogs (or muteins) thereof having an activity exhibited by the native molecule (i.e., OX2R muteins that bind specifically to CD200, or to OX2R-specific antibodies; soluble forms thereof that inhibit CD200-induced signaling through OX2R). Such proteins are substantially free of contaminating endogenous materials and, optionally, without associated native-pattern glycosylation. Derivatives of OX2R within the scope of the invention also include various structural forms of the primary protein which retain biological activity. Due to the presence of ionizable amino and carboxyl groups, for example, an OX2R protein may be in the form of acidic or basic salts, or may be in neutral form. Individual amino acid residues may also be modified by oxidation, reduction, or isomerization. The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Derivatives of OX2R may also be obtained by the action of cross-linking agents, such as M-maleimidobenzoyl succinimide ester and N-hydroxysuccinimide, at cysteine and lysine residues. The inventive proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, the proteins may be used to selectively bind (for purposes of assay or purification) antibodies raised against the proteins or against other proteins which are similar to OX2R, as well as other proteins that bind OX2R or homologs thereof.

Soluble forms of OX2R are also within the scope of the invention. The nucleotide and predicted amino acid sequence of the full-length human OX2R is shown in SEQ ID NOs:1 and 2. Computer analysis indicated that the protein has an N-terminal signal peptide; the predicted cleavage site follows residue 24. Those skilled in the art will recognize that the actual cleavage site may be different than that predicted by computer analysis. Thus, the N-terminal amino acid of the cleaved peptide is expected to be within about ten, usually within about five, amino acids on either side of the predicted, preferred cleavage site following residue 24. The signal peptide is predicted to be followed by a 242 amino acid extracellular domain, a 20 amino acid transmembrane domain (amino acids 266 through 285 of SEQ ID NO:2), and a 63 amino acid cytoplasmic tail. Alternatively, alignment of human OX2R with rat and murine OX2R predicts a 22 amino acid transmembrane domain (amino acids 266 through 287 of SEQ ID NO:2), and a 61 amino acid cytoplasmic tail.

Soluble OX2R comprises the signal peptide and the extracellular domain or a fragment thereof. Alternatively, a different signal peptide can be substituted for the native leader, beginning with residue 1 and continuing through a residue selected from the group consisting of amino acids 19 through 29 (inclusive) of SEQ ID NOs:2, 4, or 6. Fragments can be prepared using known techniques to isolate a desired portion of the extracellular region, and can be prepared, for example, by comparing the extracellular region with those of other members of the Immunoglobulin Superfamily and selecting forms similar to those prepared for other family members. Alternatively, unique restriction sites or PCR techniques that are known in the art can be used to prepare numerous truncated forms which can be expressed and analyzed for activity.

Other derivatives of the OX2R proteins within the scope of this invention include covalent or aggregative conjugates of the proteins or their fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions can comprise peptides added to facilitate purification or identification (referred to as 'tags') of OX2R proteins and homologs (e.g., poly-His). The amino acid sequence of the inventive proteins can also be linked to an identification peptide such as that described by Hopp et al., *Bio/Technology* 6:1204 (1988). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli*. Additional, useful tag proteins include green fluorescent protein (GFP; Chalfie et al., *Science* 263:802, 1994), an N-terminal peptide that contains recognition sites for a monoclonal antibody, a specific endopeptidase, and a site-specific protein kinase (PKA; Blanar and Rutter, *Science* 256:1014, 1992), birA (Altman et al., *Science* 274:94, 1996) and glutathione S transferase (GST: Smith and Johnson, *Gene* 67:31, 1988).

Fusion proteins further comprise the amino acid sequence of an OX2R linked to an immunoglobulin Fc region. Fragments of an Fc region may also be used, as can Fc muteins. For example, certain residues within the hinge region of an Fc region are critical for high affinity binding to Fc receptors; mutations changing or eliminating such residues (alone or in combination) can be made in an Fc region to decrease the affinity of the Fc for Fc receptor. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four OX2R regions.

In another embodiment, OX2R proteins further comprise an oligomerizing peptide such as a zipper domain. Zipper domain is a term used to refer to a conserved peptide domain present in these (and other) proteins, which is responsible for oligomerization of the proteins. The zipper domain (also referred to herein as an oligomerizing, or oligomer-forming, domain) comprises a repetitive heptad repeat, with four or five leucine, isoleucine or valine residues interspersed with other amino acids. Numerous examples of zipper domains are known in the art, as are methods of making oligomeric proteins using them (see U.S. Pat. No. 5,716,805, issued Feb. 10, 1998).

Also included within the scope of the invention are fragments or derivatives of the intracellular domain of OX2R. Such fragments are prepared by any of the herein-mentioned techniques, and include peptides that are identical to the cytoplasmic domain of OX2R as shown in SEQ ID NO:2 (amino acids 286 through 348), and those that comprise a portion of the cytoplasmic region. All techniques used in preparing soluble forms may also be used in preparing fragments or analogs of the cytoplasmic domain (i.e., RT-PCR techniques or use of selected restriction enzymes to prepare truncations). Nucleic acids encoding all or a fragment of the cytoplasmic domain will be useful in identifying other proteins that are associated with OX2R signaling, for example using the immunoprecipitation techniques described herein, or another technique such as a yeast two-hybrid system (Rothe et al., supra).

The present invention also includes OX2R with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of nucleic acids encoding the inventive proteins in bacteria such as *E. coli* provides non-glycosylated molecules. Functional mutant analogs of OX2R protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$. The N-linked glycosylation sites in human OX2R are shown in FIG. 1.

OX2R protein derivatives may also be obtained by mutations of the native OX2R or subunits thereof. An OX2R mutated protein, as referred to herein, is a polypeptide homologous to a native OX2R protein, respectively, but which has an amino acid sequence different from the native protein because of from one to ten amino acid deletions, insertions or substitutions. The effect of any mutation made in a nucleic acid encoding a mutated peptide may be easily determined by analyzing the ability of the mutated peptide to bind CD200 in a specific manner. Moreover, activity of OX2R analogs, muteins or derivatives can be determined by any of the assays described herein.

Analogs of the inventive proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

When a deletion or insertion strategy is adopted, the potential effect of the deletion or insertion on biological activity should be considered. Subunits of the inventive proteins may be constructed by deleting terminal or internal residues or sequences. Soluble forms of OX2R can be readily prepared and tested for their ability to inhibit binding of CD200 with OX2R. Polypeptides corresponding to the cytoplasmic regions, and fragments thereof can be prepared by similar techniques. Additional guidance as to the types of mutations that can be made is provided by a comparison of the sequence of OX2R to proteins that have similar structures, as well as by performing structural analysis of the inventive OX2R proteins.

Generally, substitutions should be made conservatively; i.e., the most preferred substitute amino acids are those which do not affect the biological activity of OX2R (i.e., ability of the inventive proteins to bind antibodies to the corresponding native protein in substantially equivalent a manner, the ability to bind the counterstructure in substantially the same manner as the native protein, or the ability to transduce an OX2R signal). Examples of conservative substitutions include substitution of amino acids outside of the binding domain(s) (either ligand/receptor or antibody binding areas for the extracellular domain, or regions that interact with other, intracellular proteins for the cytoplasmic domain), and substitution of amino acids that do not alter the secondary and/or tertiary structure of the native protein. Additional examples include substituting one aliphatic residue for another, such as Ile, Val, Leu, or Ala for one another, or substitutions of one polar residue for another, such as between Lys and Arg; Glu and Asp; or Gin and Asn. Other such conservative substitutions, for example, substitutions of entire regions having similar hydrophobicity characteristics, are well known.

Mutations in nucleotide sequences constructed for expression of analog proteins or fragments thereof must, of course, preserve the reading frame phase of the coding sequences and preferably will not create complementary regions that could hybridize to produce secondary mRNA structures such as loops or hairpins which would adversely affect translation of the mRNA.

Not all mutations in the nucleotide sequence which encodes an OX2R protein or fragments thereof will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Although a mutation site may be predetermined, it is not necessary that the nature of the mutation per se be predetermined. For example, in order to select for optimum characteristics of mutants, random mutagenesis may be conducted and the expressed mutated proteins screened for the desired activity. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques, Jan.* 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Other embodiments of the inventive proteins include OX2R polypeptides encoded by nucleic acids capable of hybridizing to the DNA of SEQ ID NO:1 under moderately stringent conditions (prewashing solution of 5×SSC, 0.5% SDS, 1.0 mM EDTA (pH 8.0) and hybridization conditions of 50° C., 5×SSC, overnight) to the nucleic acid sequences encoding OX2R, or more preferably under stringent conditions (for example, hybridization in 6×SSC at 63° C. overnight; washing in 3×SSC at 55° C.), and other sequences which are degenerate to those which encode the OX2R. In one embodiment, OX2R polypeptides are at least about 70% identical in amino acid sequence to the amino acid sequence of native OX2R protein as set forth in SEQ ID NO:2. In a preferred embodiment, OX2R polypeptides are at least about 80% identical in amino acid sequence to the native form of OX2R; more preferred polypeptides are those that are at least about 90% identical to native OX2R; most preferred polypeptides are those that are at least about 95% identical to native OX2R.

Percent identity may be determined by visual inspection and mathematical calculation, or by using a computer program. Preferably, the comparison is done using a computer program. An exemplary, preferred computer program is the Genetics Computer Group (GCG; Madison, Wis.) Wisconsin package version 10.0 program, 'GAP.' The preferred default parameters for the 'GAP' program includes: (1) The GCG implementation of the previously stated comparison matrixes for nucleotides and amino acids; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by one skilled in the art of sequence comparison may also be used. For fragments derived from the OX2R protein, the identity is calculated based on that portion of the OX2R protein that is present in the fragment The biological activity of OX2R analogs or muteins can be determined by testing the ability of the analogs or muteins to bind OX2/CD200, for example. Suitable assays, for example, an enzyme immunoassay or a dot blot, employing an antibody that binds native OX2R, or a soluble form of CD200, can be used to assess the activity of OX2R analogs or muteins, as can assays that employ cells expressing CD200. Suitable assays also include, for example, signal transduction assays and methods that evaluate the ability of the cytoplasmic region of OX2R to associate with other intracellular proteins involved in signal transduction will also be useful to assess the activity of OX2R analogs or muteins. Such methods are well known in the art.

Fragments of the OX2R nucleotide sequences are also useful. In one embodiment, such fragments comprise at least about 17 consecutive nucleotides, preferably at least about 25 nucleotides, more preferably at least 30 consecutive nucleotides, of the OX2R nucleic acid disclosed herein. DNA and RNA complements of such fragments are provided herein, along with both single-stranded and double-stranded forms of the OX2R nucleic acid of SEQ ID Nos:1, 3, or 5, and those encoding the aforementioned polypeptides. A fragment of OX2R nucleic acid generally comprises at least about 17 nucleotides, preferably from about 17 to about 30 nucleotides. Such nucleic acid fragments (for example, a probe corresponding to the extracellular domain of OX2R) are used as a probe or as primers in a polymerase chain reaction (PCR).

The probes also find use in detecting the presence of OX2R nucleic acids in in vitro assays and in such procedures as Northern and Southern blots. Cell types expressing OX2R can be identified as well. Such procedures are well known, and the skilled artisan can choose a probe of suitable length, depending on the particular intended application. For PCR, 5' and 3' primers corresponding to the termini of a desired OX2R nucleic acid sequence are employed to amplify that sequence, using conventional techniques.

Other useful fragments of the OX2R nucleic acids are antisense or sense oligonucleotides comprising a single-stranded nucleic acid sequence (either RNA or DNA) capable of binding to target OX2R mRNA (sense) or OX2R DNA (antisense) sequences. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

In certain other embodiments of the invention, antagonists can be designed to reduce the level of endogenous OX2R gene expression, e.g., using well-known antisense or ribozyme approaches to inhibit or prevent translation of OX2R mRNA transcripts; triple helix approaches to inhibit transcription of OX2R family genes; or targeted homologous recombination to inactivate or "knock out" the OX2R genes or their endogenous promoters or enhancer elements. Such antisense, ribozyme, and triple helix antagonists can be designed to reduce or inhibit either unimpaired, or if appropriate, mutant OX2R gene activity. Techniques for the production and use of such molecules are well known to those of skill in the art.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a OX2R mRNA. The antisense oligonucleotides will bind to the complementary target gene mRNA transcripts and prevent translation. Absolute complementarity, although preferred, is not required. A sequence "complementary" to a portion of a nucleic acid, as referred to herein, means a sequence having sufficient complementarity to be able to hybridize with the nucleic acid, forming a stable duplex (or triplex, as appropriate). In the case of double-stranded antisense nucleic acids, a single strand of the duplex DNA can thus be tested, or triplex formation can be assayed. The ability to hybridize will depend on both the degree of complementarity and the length of the antisense nucleic acid. Preferred oligonucleotides are complementary to the 5' end of the message, e.g., the 5' untranslated sequence up to and including the AUG initiation codon. However, oligonucleotides complementary to the 5'- or 3'-non-translated, non-coding regions of the OX2R gene transcript, or to the coding regions, could be used in an antisense approach to inhibit translation of endogenous OX2R mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The oligonucleotides can be DNA or RNA or chimeric mixtures or derivatives or modified versions thereof, single-stranded or double-stranded. Chimeric oligonucleotides, oligonucleosides, or mixed oligonucleotides/oligonucleosides of the invention can be of several different types. These include a first type wherein the "gap" segment of nucleotides is positioned between 5' and 3' "wing" segments of linked nucleosides and a second "open end" type wherein the "gap" segment is located at either the 3' or the 5' terminus of the oligomeric compound (see, e.g., U.S. Pat. No. 5,985,664). Oligonucleotides of the first type are also known in the art as "gapmers" or gapped oligonucleotides. Oligonucleotides of the second type are also known in the art as "hemimers" or "wingmers".

The oligonucleotide can be modified at the base moiety, sugar moiety, or phosphate backbone, for example, to improve stability of the molecule, hybridization, etc. The oligonucleotide can include other appended groups such as peptides (e.g., for targeting host cell receptors in vivo), or agents facilitating transport across the cell membrane (see, e.g., Letsinger et al., 1989, *Proc Natl Acad Sci USA* 86: 6553–6556; Lemaitre et al., 1987, *Proc Natl Acad Sci USA* 84: 648–652; PCT Publication No. WO88/09810), or hybridization-triggered cleavage agents or intercalating agents. (See, e.g., Zon, 1988, *Pharm. Res.* 5: 539–549).

The antisense molecules should be delivered to cells which express the OX2R transcript in vivo. A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface) can be administered systemically. However, it is often difficult to achieve intracellular concentrations of the antisense sufficient to suppress translation of endogenous mRNAs.

A preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous OX2R gene transcripts and thereby prevent translation of the OX2R mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Ribozyme molecules designed to catalytically cleave OX2R mRNA transcripts can also be used to prevent translation of OX2R mRNA and expression of OX2R polypeptides. (See, e.g., PCT International Publication WO90/11364 and U.S. Pat. No. 5,824,519). The ribozymes that can be used in the present invention include hammerhead ribozymes (Haseloff and Gerlach, 1988, Nature, 334:585–591), RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (International Patent Application No. WO 88/04300; Been and Cech, 1986, Cell, 47:207–216). As in the antisense approach, the ribozymes can be composed of modified oligonucleotides (e.g. for improved stability, targeting, etc.) and should be delivered to cells which express the OX2R polypeptide in vivo. A preferred method of delivery involves using a DNA construct "encoding" the ribozyme under the control of a strong constitutive pol III or pol II promoter, so that transfected cells will produce sufficient quantities of the ribozyme to destroy endogenous OX2R messages and inhibit translation. Because ribozymes, unlike antisense molecules, are catalytic, a lower intracellular concentration is required for efficiency.

Alternatively, endogenous OX2R gene expression can be reduced by targeting deoxyribonucleotide sequences complementary to the regulatory region of the target gene (i.e., the target gene promoter and/or enhancers) to form triple helical structures that prevent transcription of the target OX2R gene. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Anti-sense RNA and DNA, ribozyme, and triple helix molecules of the invention can be prepared by any method known in the art for the synthesis of DNA and RNA molecules. These include techniques for chemically synthesizing oligodeoxy-ribonucleotides and oligoribonucleotides well known in the art such as for example solid phase phosphoramidite chemical synthesis. Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448–7451).

Alternatively, RNA molecules can be generated by in vitro and in vivo transcription of DNA sequences encoding the antisense RNA molecule. Such DNA sequences can be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene.

Such approaches are particularly suited in the agricultural field where modifications to ES (embryonic stem) cells can be used to generate animal offspring with an inactive target gene (e.g., see Thomas and Capecchi, 1987 and Thompson, 1989, supra), or in model organisms such as Caenorhabditis elegans where the "RNA interference" ("RNAi") technique (Grishok, Tabara, and Mello, 2000, Science 287 (5462): 2494–2497), or the introduction of transgenes (Dernburg et al., 2000, Genes Dev. 14 (13): 1578–1583) are used to inhibit the expression of specific target genes. However this approach can be adapted for use in humans provided the recombinant DNA constructs are directly administered or targeted to the required site in vivo using appropriate vectors such as viral vectors.

Uses of Nucleic Acids, Proteins and Analogs

The OX2R nucleic acids, proteins and analogs described herein will have numerous uses, including the preparation of pharmaceutical compositions. For example, soluble forms of OX2R will be useful as antagonists of the interaction between membrane-bound OX2R and its counterstructure/ligand Ox2/CD200. Soluble forms of OX2R can also be used to detect or enumerate cells expressing OX2/CD200, and to deliver selected agents to such cells, in much the same way that antibodies to OX2/CD200 are used. Similarly, soluble OX2R can be used or tissue samples, to type or enumerate cells therein. OX2R compositions (both protein and nucleic acids) will also be useful in development of both agonistic and antagonistic antibodies to OX2R.

The inventive proteins will also be useful in preparing kits that are used to detect soluble OX2R or CD200, or monitor OX2R-related activity, for example, in patient specimens. OX2R proteins will also find uses in monitoring OX2R-related activity in other samples or compositions, as is necessary when screening for antagonists or mimetics of this activity (for example, peptides or small molecules that inhibit or mimic, respectively, the interaction). A variety of assay formats are useful in such kits, including (but not limited to) ELISA, dot blot, solid phase binding assays (such as those using a biosensor), rapid format assays and bioassays.

The purified OX2R according to the invention will facilitate the discovery of agonists and/or antagonists of OX2R, and thus, agents that are capable of modulating an immune response. The use of a purified OX2R polypeptide in the screening for potential agonists and/or antagonists is important and can virtually eliminate the possibility of interfering reactions with contaminants. Such a screening assay can utilize either the extracellular domain of OX2R, the intracellular domain, or a fragment of either of these polypeptides. Detecting the inhibitory or agonistic activity of a molecule would typically involve use of a soluble form of OX2R derived from the extracellular domain in a screening assay to detect molecules capable of binding OX2R, or using a polypeptide derived from the intracellular domain in an assay to detect inhibition or enhancement of the interaction of OX2R and other, intracellular proteins involved in signal transduction.

Moreover, in vitro systems can be used to ascertain the ability of molecules to antagonize or agonize OX2R activity. Included in such methods are uses of OX2R chimeras, for example, a chimera of the OX2R intracellular domain and an extracellular domain derived from a protein having a known ligand. The effects on signal transduction of various molecule can then be monitored by utilizing the known ligand to transduce a signal.

In addition, OX2R polypeptides can also be used for structure-based design of OX2R agonists and/or antagonists. Such structure-based design is also known as "rational drug design." The OX2R polypeptides can be three-dimensionally analyzed by, for example, X-ray crystallography, nuclear magnetic resonance or homology modeling, all of which are well-known methods. The use of OX2R structural information in molecular modeling software systems to assist in inhibitor design is also encompassed by the invention. Such computer-assisted modeling and drug design may utilize information such as chemical conformational analysis, electrostatic potential of the molecules, protein folding, etc. A particular method of the invention comprises analyzing the three dimensional structure of OX2R for likely binding sites of substrates, synthesizing a new molecule that incorporates a predictive reactive site, and assaying the new molecule as described above.

The inventive nucleic acids are useful for the expression of recombinant proteins, and as probes for analysis (either quantitative or qualitative) of the presence or distribution of OX2R transcripts. The inventive nucleic acids are also useful in gene therapy techniques, for replacement of defective OX2R DNA, or in treatment of infectious or neoplastic disease conditions in which it is useful to have cells expressing additional OX2R. For such uses, the alternatively spliced, soluble versions disclosed herein can be made cell associated by a transmembrane domain and cytoplasmic region, for example, those present in the full-length form of OX2R disclosed herein. Additional amino acids can be added between the transmembrane region and the extracellular domain to facilitate folding and/or activity of the resulting membrane-associated receptor. Preferably, the amino acids to be added correspond to those present in the full-length from but missing in the soluble forms.

Expression of Recombinant OX2R

The proteins of the present invention are preferably produced by recombinant DNA methods by inserting a nucleic acid sequence encoding OX2R protein or an analog thereof into a recombinant expression vector and expressing the nucleic acid sequence in a recombinant expression system under conditions promoting expression. Nucleic acid sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived nucleic acid fragments encoding OX2R, or homologs, muteins or bioequivalent analogs thereof, operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Nucleic acid sequences encoding OX2R, or homologs or analogs thereof which are to be expressed in a microorganism will preferably contain no introns that could prematurely terminate transcription of DNA into mRNA.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986). A preferred eukaryotic vector for expression of OX2R DNA is referred to as pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter.

Host Cells

Transformed host cells are cells which have been transformed or transfected with expression vectors constructed using recombinant DNA techniques and which contain sequences encoding the proteins of the present invention. Transformed host cells may express the desired protein (OX2R, or homologs or analogs thereof), but host cells transformed for purposes of cloning or amplifying the inventive DNA do not need to express the protein. Expressed proteins will preferably be secreted into the culture supernatant, depending on the DNA selected, but may be deposited in the cell membrane.

Suitable host cells for expression of proteins include prokaryotes, yeast or higher eukaryotic cells under the control of appropriate promoters. Prokaryotes include gram negative or gram positive organisms, for example *E. coli* or *Bacillus* spp. Higher eukaryotic cells include established cell lines of mammalian origin as described below. Cell-free translation systems could also be employed to produce proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotic expression hosts may be used for expression of OX2R, or homologs or analogs thereof that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera *Pseudomonas, Streptomyces*, and *Staphylococcus*, although others may also be employed as a matter of choice.

Recombinant OX2R may also be expressed in yeast hosts, preferably from the *Saccharomyces* species, such as *S. cerevisiae*. Yeast of other genera, such as *Pichia* or *Kluyveromyces* may also be employed. Yeast vectors will generally contain an origin of replication from the 2μ yeast plasmid or an autonomously replicating sequence (ARS), promoter, DNA encoding the protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art; an exemplary technique is described by Hinnen et al., *Proc. Natl. Acad. Sci. USA* 75:1929, 1978, selecting for Trp⁺ transformants in a selective medium consisting of 0.67% yeast nitrogen base, 0.5% casamino acids, 2% glucose, 10 µg/ml adenine and 20 µg/ml uracil. Host strains transformed by vectors comprising the ADH2 promoter may be grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purification of Recombinant OX2R

Purified OX2R, and homologs or analogs thereof are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following the concentration step, the concentrate can be applied to a suitable purification matrix. For example, a suitable affinity matrix can comprise a counter structure protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying the inventive proteins.

Affinity chromatography is a particularly preferred method of purifying OX2R and homologs thereof. For example, an OX2R expressed as a fusion protein comprising an immunoglobulin Fc region can be purified using Protein A or Protein G affinity chromatography. Moreover, an OX2R protein comprising an oligomerizing zipper domain may be purified on a resin comprising an antibody specific to the oligomerizing zipper domain. Monoclonal antibodies against the OX2R protein may also be useful in affinity chromatography purification, by utilizing methods that are well-known in the art. A ligand may also be used to prepare an affinity matrix for affinity purification of OX2R.

Finally, one or more reversed-phase high performance liquid chromatography (RP-HPLC) steps employing hydrophobic RP-HPLC media, e.g., silica gel having pendant methyl or other aliphatic groups, can be employed to further purify an OX2R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant protein can be disrupted by any convenient method, including freeze-thaw cycling, sonication, mechanical disruption, or use of cell lysing agents.

Fermentation of yeast which express the inventive protein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Protein synthesized in recombinant culture is characterized by the presence of cell components, including proteins, in amounts and of a character which depend upon the purification steps taken to recover the inventive protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of the inventive proteins free of other proteins which may be normally associated with the proteins as they are found in nature in the species of origin.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide or a nucleic acid encoding a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*Proc. Natl. Acad. Sci. USA* 84:3439, 1987), Larrick et al. (*Bio/Technology* 7:934, 1989), and Winter and Harris (TIPS 14:139, May, 1993).

In addition to antibodies that can be produced via recombinant methods, human antibodies can be produced in animals that have been genetically manipulated to have human immunoglobulin genes (transgenic animals). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')2 fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Uses and Administration of OX2R Compositions

The present invention provides methods of using therapeutic compositions comprising an effective amount of a protein and a suitable diluent and carrier, and methods for regulating an immune or inflammatory response. The use of OX2R in conjunction with soluble cytokine receptors or cytokines, or other immunoregulatory molecules is also contemplated.

For therapeutic use, purified protein is administered to a patient, preferably a human, for treatment in a manner appropriate to the indication. Thus, for example, OX2R protein compositions administered to regulate immune function can be given by bolus injection, continuous infusion, sustained release from implants, or other suitable technique. Typically, a therapeutic agent will be administered in the form of a composition comprising purified OX2R, in conjunction with physiologically acceptable carriers, excipients or diluents. Such carriers will be nontoxic to recipients at the dosages and concentrations employed.

Ordinarily, the preparation of such protein compositions entails combining the inventive protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

Screening Assays Using OX2R Compositions:

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked immunosorbant assays (ELISA) or radioimmunoassays. Also comprehended herein are cell-based assays, for example those utilizing reporter genes, as well as functional assays that analyze the effect of an antagonist or agonist on biological function(s).

Moreover, combinations of screening assays can be used to find molecules that regulate the biological activity of OX2R. Molecules that regulate the biological activity of a polypeptide may be useful as agonists or antagonists of the peptide. In using combinations of various assays, it is usually first determined whether a candidate molecule binds to a polypeptide by using an assay that is amenable to high throughput screening. Binding candidate molecules identified in this manner are then added to a biological assay to determine biological effects. Molecules that bind and that have an agonistic or antagonistic effect on biologic activity will be useful in treating or preventing disease or conditions with which the polypeptide(s) are implicated.

Homogeneous assays are mix-and-read style assays that are very amenable to robotic application, whereas heterogeneous assays require separation of free from bound analyte by more complex unit operations such as filtration, centrifugation or washing. These assays are utilized to detect a wide variety of specific biomolecular interactions (including protein-protein, receptor-ligand, enzyme-substrate, and so on), and the inhibition thereof by small organic molecules. These assay methods and techniques are well known in the art (see, e.g., High Throughput Screening: The Discovery of Bioactive Substances, John P. Devlin (ed.), Marcel Dekker, New York, 1997 ISBN: 0-8247-0067-8). The screening assays of the present invention are amenable to high throughput screening of chemical libraries and are suitable for the identification of small molecule drug candidates, antibodies, peptides, and other antagonists and/or agonists, natural or synthetic.

One such assay is based on fluorescence resonance energy transfer (FRET; for example, HTRF®, Packard Instrument Company, Meriden, Conn.; LANCE™, PerkinElmer LifeSciences, Wallac Oy., Turku, Finland) between two fluorescent labels, an energy donating long-lived chelate label and a short-lived organic acceptor. The energy transfer occurs when the two labels are brought in close proximity via the molecular interaction between OX2R and OX2/CD200. In a FRET assay for detecting inhibition of the binding of OX2R and OX2/CD200, europium chelate or cryptate labeled OX2R or OX2/CD200 serves as an energy donor and streptavidin-labeled allophycocyanin (APC) bound to the appropriate binding partner (i.e., OX2R if OX2/CD200 is labeled, or OX2/CD200 if OX2R is labeled) serves as an energy acceptor. Once OX2R binds OX2/CD200, the donor and acceptor molecules are brought in close proximity, and energy transfer occurs, generating a fluorescent signal at 665 nm. Antagonists of the interaction of OX2R and OX2/CD200 will thus inhibit the fluorescent signal, whereas agonists of this interaction would enhance it.

DELFIA® (dissociated enhanced lanthamide fluoroimmunoassay; PerkinElmer LifeSciences, Wallac Oy., Turku, Finland) is a solid-phase assay based on time-resolved fluorometry analysis of lanthamide chelates (see, for example, U.S. Pat. No. 4,565,790, issued Jan. 21, 1986). For this type of assay, microwell plates are coated with a first protein (OX2R or OX2/CD200). The binding partner (OX2/CD200 or OX2R, respectively) is conjugated to europium chelate or cryptate, and added to the plates. After suitable incubation, the plates are washed and a solution that dissociates europium ions from solid phase bound protein, into solution, to form highly fluorescent chelates with ligands present in the solution, after which the plates are read using a reader such as a VICTOR$^2$™ (PerkinElmer LifeSciences, Wallac Oy., Turku, Finland) plate reader to detect emission at 615 nm).

Another assay that will be useful in the inventive methods is a FlashPlate® (Packard Instrument Company, IL)-based assay. This assay measures the ability of compounds to inhibit protein-protein interactions. FlashPlates® are coated with a first protein (either OX2R or OX2/CD200), then washed to remove excess protein. For the assay, compounds to be tested are incubated with the second protein (OX2/CD200, if the plates are coated with OX2R, or OX2R if plates are coated with OX2/CD200) and I125 labeled antibody against the second protein and added to the plates. After suitable incubation and washing, the amount of radioactivity bound is measured using a scintillation counter (such as a MicroBeta® counter; PerkinElmer LifeSciences, Wallac Oy., Turku, Finland).

The AlphaScreen™ assay (Packard Instrument Company, Meriden, Conn.). AlphaScreen™ technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of OX2R and OX2/CD200), the singlet-state oxygen molecules reacts with chemiluminescent groups in the acceptor beads, which immediately transfer energy to fluorescent acceptors in the same bead. These fluorescent acceptors shift the emission wavelength to 520–620 nm, resulting in a detectable signal. Antagonists of the interaction of OX2R with OX2/CD200 will thus inhibit the shift in emission wavelength, whereas agonists of this interaction would enhance it.

One embodiment of a method for identifying molecules which inhibit or antagonize OX2R-mediated signaling involves adding a candidate molecule to a medium which contains cells that express OX2R; changing the conditions of said medium so that, but for the presence of the candidate molecule, OX2R would be bound to OX2/CD200, and observing the binding and stimulation or inhibition of a functional response. The activity of the cells that were contacted with the candidate molecule may then be compared with the identical cells that were not contacted and antagonists and agonists of the polypeptides of the instant invention may be identified. The measurement of biological activity may be performed by a number of well-known methods such as measuring the amount of protein present (e.g. an ELISA) or of the protein's activity. A decrease in biological stimulation or activation would indicate an antagonist. An increase would indicate an agonist.

Computer Analysis of Assay Results

In one aspect of the invention, the assays of the invention are used to identify compounds that alter OX2R signaling activity. The benefits of integrated robotic systems used to analyze collections of chemical compounds/natural products in such assays, which preferably incorporate high-throughput screening methods, are most often realized by the use of sophisticated computer and statistical techniques to manage the resulting data. In one form, the information generated in the inventive screening assays is stored (or compiled) in electronic form, using a computerized database that allows information to be efficiently catalogued and retrieved. Such databases are comprised of records, usually one record for each compound, that includes information about the compound, such as chemical name, structure, source, activity in a binding assay, activity in a biological assay, etc.

The information may be entered into the database manually, that is by a user entering data through a user interface (i.e., keyboard, touchpad, etc.), or it may be entered electronically as in when a robotic system for analysis of compounds generates electronic results that are transferred to another computer system (often referred to as uploading). Such information is usually stored in a discrete area of the record referred to as a field. Additionally, the information, preferably in the form of a database, may be stored permanently or temporarily on various forms of storage media, including paper, the brains of living organisms, compact disks, floppy disks, magnetic tapes, optical tapes, hard drives, computer system memory units, and the like.

The database may be stand-alone, or the records therein may be related to other databases (a relational database). Examples of other databases include publicly available, well-known databases such as GenBank for peptides and nucleic acids (and associated databases maintained by the National Center for Biotechnology Information or NCBI), and the databases available through www.chemfinder.com or The Dialog Corporation (Cary, N.C.) for chemical compounds.

A user will be able to search the database according to the information recorded (selecting records that have a particular value in a selected field, for example, searching for all compounds that inhibited a binding assay by at least about 30%); accordingly, another aspect of the invention is a method of using a computer system to catalog and store information about various chemical compounds. The ability to store and retrieve such information in computerized form allows those of ordinary skill in the art to select compounds for additional testing, including additional analysis of binding ability, biological testing, and testing in animal models or clinical trials of pharmaceutical agents in humans. Moreover, in addition to storing and cataloging information, the database can be used to provide a report, either in electronic form or in the form of a printout, that will facilitate further analysis of selected compounds.

One embodiment of the invention comprises a computing environment; an input device, connected to the computing environment, to receive information from the user; an output device, connected to the computing environment, to provide information to the user; and a plurality of algorithms selectively executed based on at least a portion of the received information, wherein any one of these algorithms analyzes at least a portion of the received information and generates output information, and preferably wherein the output information is communicated via the output device. The computing environment preferably further comprises a communications network; a server connected to the network; and a client connected to the network, wherein the client is part of a client-server architecture and typically is an application that runs on a personal computer or workstation and relies on a server to perform some operations (see Nath, 1995, The Guide To SQL Server, 2nd ed., Addison-Wesley Publishing Co.).

The computing environment of the present invention is advantageously implemented using any multipurpose computer system including those generally referred to as personal computers and mini-computers. Such a computer system will include means for processing input information such as at least one central processor, for example an Intel® processor (including Pentium® Pentium® II, Celeron™, Pentium® II3, Pentium® 4 or the like), or Motorola processor (for example, a PowerPC G3 or PowerPC G4 microprocessor capable of running at speeds up to 533 MHz or higher); a storage device, such as a hard disk, for storing information related to OX2R and/or OX2/CD200 polypeptides and/or compounds that alter the binding of OX2R and OX2/CD200 (or signaling through OX2R); and means for receiving input information. Those of skill in the art will recognize that computer technology is changing at a rapid rate; accordingly, new, improved versions of processors are comprehended herein.

The processor, which comprises and/or accesses memory units of the computer system, is programmed to perform analyses of information related to the OX2R and/or OX2/CD200 polypeptides and/or compounds that modulate their binding (or signaling through OX2R). This programming may be permanent, as in the case where the processor is a dedicated PROM (programmable read-only memory) or EEPROM (electrically erasable programmable read-only memory), or it may be transient in which case the programming instructions are loaded from the storage device or from a floppy diskette or other transportable computer-readable media. The computing environment further preferably comprises a user interface such as a Unix/X-Window interface, a Microsoft Windows interface, or a Macintosh operating system interface.

Preferably, the computing environment further includes an optical disk for storing data, a printer for providing a hard copy of the data, and a monitor or video display unit to facilitate user input of information and to display both input and output information. The output information may be output from the processor within the computer system in print form using a printer; on a video display unit; or via a communications link or network to another processor or client application.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

A novel cDNA was identified by subtractive hybridization of cDNAs derived from human dendritic cell (DC) versus cDNAs derived from monocytes (both derived from Flt3-ligand (FL)-treated healthy volunteers); two alternate forms were identified by polymerase chain reaction (PCR). SEQ ID NO:1 shows the nucleotide and amino acid sequence of the full-length protein; the nucleotide and amino acid sequences of the two alternate, soluble forms are shown in SEQ ID NOs:3 and 5.

cDNAs encoding similar forms of OX2R were isolated from DC-enriched cells (spleen cells were isolated from a mouse treated with FL, and treated to remove non-DC; the enriched population was approximately 45% DC) by RT-PCR using primers based on the full-length form of OX2R; the nucleotide and amino acids are shown in SEQ ID NOs:7, 9 and 11, and an alignment of the forms of mOX2R is presented in FIG. 3. The predicted signal peptide of mOX2R comprises amino acids 1 through 23, although those of skill in the art recognize that the actual cleavage site may vary by five, or up to ten, amino acids from that predicted.

The variant OX2R represented by SEQ ID NO:9 has a deletion of virtually the entire V region; those of skill in the art readily recognize that other, similar versions of OX2 lacking all or part of the V region can be made. These include polypeptides having the amino acid sequence of SEQ ID NOs:7 or 11 or fragments thereof, wherein the amino terminus is an amino acid between 1 and 155 (more preferably between 1 and 150; most preferably between 145 and 155) of SEQ ID NOs:7 or 11. Orthologous versions of human OX2R include polypeptides having the amino acid sequence of SEQ ID NOs:1, 3 or 5 or fragments thereof, wherein the amino terminus is an amino acid between 1 and 181 (more preferably between 1 and 177; most preferably between 171 and 181) of SEQ ID NOs:1, 3 or 5. Those of ordinary skill in the art will also realize that the actual amino terminus may vary by up to five amino acids from these.

EXAMPLE 2

This example describes construction of an OX2R nucleic acid construct to express an OX2R/Fc fusion protein. A soluble form of human OX2R fused to the Fc region of human IgG$_1$ was constructed in the mammalian expression vector pDC412, a vector derived by reversing the orientation of the Bgl 2 and Not 1 sites in pDC409. The expression vector designated pDC409 is a mammalian expression vector derived from the pDC406 vector described in McMahan et al. (*EMBO J.* 10:2821–2832, 1991; hereby incorporated by reference). Features added to pDC409 (compared to pDC406) include additional unique restriction sites in the multiple cloning site (mcs); three stop codons (one in each reading frame) positioned downstream of the mcs; and a T7 polymerase promoter, downstream of the mcs, that facilitates sequencing of nucleic acid inserted into the mcs.

To obtain OX2R/Fc protein, an OX2R/Fc expression plasmid is transfected into CV-1/EBNA cells, and supernatants are collected for about one week. The OX2R/Fc fusion protein is purified by means well-known in the art for purification of Fc fusion proteins, for example, by protein A Sepharose column chromatography according to manufacturer's recommendations (i.e., Pharmacia, Uppsala, Sweden). Amino acid sequencing of purified OX2R/Fc protein yielded an N-terminal amino acid sequence of Ala Ala Gln Pro Asn Asn Ser Leu Met Leu (corresponding to amino acids 27 through 36 of SEQ ID NO:2).

EXAMPLE 3

This example illustrates the preparation of monoclonal antibodies against OX2R. Preparations of purified recombinant OX2R, for example, or transfected cells expressing high levels of OX2R, are employed to generate monoclonal antibodies against OX2R using conventional techniques, such as those disclosed in U.S. Pat. No. 4,411,993. DNA encoding OX2R can also be used as an immunogen, for example, as reviewed by Pardoll and Beckerleg in *Immunity* 3:165, 1995. Such antibodies are likely to be useful in interfering with OX2R-induced signaling (antagonistic or blocking antibodies) or in inducing a signal by cross-linking OX2R (agonistic antibodies), as components of diagnostic or research assays for OX2R or OX2R activity, or in affinity purification of OX2R.

To immunize rodents, OX2R immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 µg subcutaneously into a selected rodent, for example, BALB/c mice or Lewis rats. DNA may be given intradermally (Raz et al., *Proc. Natl. Acad. Sci. USA* 91:9519, 1994) or intamuscularly (Wang et al., *Proc. Natl. Acad. Sci. USA* 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with OX2R, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144:4212 (1990). Positive clones are then injected into the peritoneal cavities of syngeneic rodents to produce ascites containing high concentrations (>1 mg/ml) of anti-OX2R monoclonal antibody.

The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to OX2R protein. Both blocking (i.e., antibodies that bind OX2R and inhibit binding of a ligand to OX2R) and non-blocking (i.e., antibodies that bind OX2R and do not inhibit ligand binding) can be isolated by these methods.

EXAMPLE 4

This example describes the chromosomal mapping of human OX2R using PCR-based mapping strategies. Initial human chromosomal assignments are made using OX2R-specific PCR primers and a BIOS Somatic Cell Hybrid PCRable DNA kit from BIOS Laboratories (New Haven, Conn.), following the manufacturer's instructions. More detailed mapping is performed using a radiation hybrid mapping panel Genebridge 4 Radiation Hybrid Panel (Research Genetics, Huntsville, Ala.; described in Walter, M A et al., *Nature Genetics* 7:22–28, 1994). Data from this analysis is then submitted electronically to the MIT Radiation Hybrid Mapper (URL: http://www-genome.wi.mit.edu/cgi-bin/contig/rhmapper.pl) following the instructions contained therein. This analysis yields specific genetic marker names which, when submitted electronically to the NCBI Entrez browser (URL: http://www3.ncbi.nlm.nih.gov/htbin-post/Entrez/query?db=c&form=0), yields the specific map locations.

EXAMPLE 5

This example describes the upregulation of CD200 by CD40 ligand (CD40L; described in U.S. Pat. No. 5,962,406, issued Oct. 5, 1999). Monocytes were obtained from healthy volunteers and cultured in GM-CSF and IL-4 for seven days, to generate monocyte-derived DC (MoDC). For activation, these cells cultured for another 24 hrs in the presence of CD40L. By PCR, CD200 expression was upregulated on the CD40L activated MoDC as compared to non-activated MoDC, indicating that CD200 plays a role in the generation and/or maintenance of an immune response.

We claim:

1. An isolated DNA encoding an OX2 receptor (OX2R) protein, selected from the group consisting of:
   (a) a DNA encoding a protein comprising amino acids x to y of SEQ ID NO:4, wherein x represents an integer from 1 to 34, inclusive, and y represents an integer from 257 to 260, inclusive; and
   (b) a DNA encoding a protein comprising amino acids x to y of SEQ ID NO:6, wherein x represents an integer from 1 to 34, inclusive, and y is 257.

2. The isolated DNA of claim 1, which further comprises a DNA encoding a polypeptide selected from the group consisting of an immunoglobulin Fc domain, an immunoglobulin Fc mutein, a tag peptide, a peptide comprising at least 6 His residues, a leucine zipper, and combinations thereof.

3. A recombinant expression vector comprising a DNA sequence according to claim 1.

4. A recombinant expression vector comprising a DNA sequence according to claim 2.

5. An isolated host cell transformed or transfected with an expression vector according to claim 3.

6. An isolated host cell transfonned or transfected with an expression vector according to claim 4.

7. A process for preparing an OX2R protein, comprising culturing a host cell according to claim 5 under conditions promoting expression and recovering the OX2R.

8. A process for preparing an OX2R protein, comprising culturing a host cell according to claim 6 under conditions promoting expression and recovering the OX2R protein.

* * * * *

SEQUENCE LISTING

<160> NUMBER OF SEQ ID NOS: 12

<210> SEQ ID NO 1
<211> LENGTH: 1047
<212> TYPE: DNA
<213> ORGANISM: Homo sapiens
<220> FEATURE:
<221> NAME/KEY: CDS
<222> LOCATION: (1)..(1047)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | ctc | tgc | cct | tgg | aga | act | gct | aac | cta | ggg | cta | ctg | ttg | att | ttg | 48 |
| Met | Leu | Cys | Pro | Trp | Arg | Thr | Ala | Asn | Leu | Gly | Leu | Leu | Leu | Ile | Leu | |
| 1 | | | | 5 | | | | | 10 | | | | | 15 | | |
| act | atc | ttc | tta | gtg | gcc | gaa | gcg | gag | ggt | gct | gct | caa | cca | aac | aac | 96 |
| Thr | Ile | Phe | Leu | Val | Ala | Glu | Ala | Glu | Gly | Ala | Ala | Gln | Pro | Asn | Asn | |
| | | | 20 | | | | | 25 | | | | | 30 | | | |
| tca | tta | atg | ctg | caa | act | agc | aag | gag | aat | cat | gct | tta | gct | tca | agc | 144 |
| Ser | Leu | Met | Leu | Gln | Thr | Ser | Lys | Glu | Asn | His | Ala | Leu | Ala | Ser | Ser | |
| | | 35 | | | | | 40 | | | | | 45 | | | | |
| agt | tta | tgt | atg | gat | gaa | aaa | cag | att | aca | cag | aac | tac | tcg | aaa | gta | 192 |
| Ser | Leu | Cys | Met | Asp | Glu | Lys | Gln | Ile | Thr | Gln | Asn | Tyr | Ser | Lys | Val | |
| | 50 | | | | | 55 | | | | | 60 | | | | | |
| ctc | gca | gaa | gtt | aac | act | tca | tgg | cct | gta | aag | atg | gct | aca | aat | gct | 240 |
| Leu | Ala | Glu | Val | Asn | Thr | Ser | Trp | Pro | Val | Lys | Met | Ala | Thr | Asn | Ala | |
| 65 | | | | | 70 | | | | | 75 | | | | | 80 | |
| gtg | ctt | tgt | tgc | cct | cct | atc | gca | tta | aga | aat | ttg | atc | ata | ata | aca | 288 |
| Val | Leu | Cys | Cys | Pro | Pro | Ile | Ala | Leu | Arg | Asn | Leu | Ile | Ile | Ile | Thr | |
| | | | | 85 | | | | | 90 | | | | | 95 | | |
| tgg | gaa | ata | atc | ctg | aga | ggc | cag | cct | tcc | tgc | aca | aaa | gcc | tac | agg | 336 |
| Trp | Glu | Ile | Ile | Leu | Arg | Gly | Gln | Pro | Ser | Cys | Thr | Lys | Ala | Tyr | Arg | |
| | | | 100 | | | | | 105 | | | | | 110 | | | |
| aaa | gaa | aca | aat | gag | acc | aag | gaa | acc | aac | tgt | act | gat | gag | aga | ata | 384 |
| Lys | Glu | Thr | Asn | Glu | Thr | Lys | Glu | Thr | Asn | Cys | Thr | Asp | Glu | Arg | Ile | |
| | | 115 | | | | | 120 | | | | | 125 | | | | |
| acc | tgg | gtc | tcc | aga | cct | gat | cag | aat | tcg | gac | ctt | cag | att | cgt | cca | 432 |
| Thr | Trp | Val | Ser | Arg | Pro | Asp | Gln | Asn | Ser | Asp | Leu | Gln | Ile | Arg | Pro | |
| | 130 | | | | | 135 | | | | | 140 | | | | | |
| gtg | gcc | atc | act | cat | gac | ggg | tat | tac | aga | tgc | ata | atg | gta | aca | cct | 480 |
| Val | Ala | Ile | Thr | His | Asp | Gly | Tyr | Tyr | Arg | Cys | Ile | Met | Val | Thr | Pro | |
| 145 | | | | | 150 | | | | | 155 | | | | | 160 | |
| gat | ggg | aat | ttc | cat | cgt | gga | tat | cac | ctc | caa | gtg | tta | gtt | aca | cct | 528 |
| Asp | Gly | Asn | Phe | His | Arg | Gly | Tyr | His | Leu | Gln | Val | Leu | Val | Thr | Pro | |
| | | | | 165 | | | | | 170 | | | | | 175 | | |
| gaa | gtg | acc | ctg | ttt | caa | aac | agg | aat | aga | act | gca | gta | tgc | aag | gca | 576 |
| Glu | Val | Thr | Leu | Phe | Gln | Asn | Arg | Asn | Arg | Thr | Ala | Val | Cys | Lys | Ala | |
| | | | 180 | | | | | 185 | | | | | 190 | | | |
| gtt | gca | ggg | aag | cca | gct | gcg | cag | atc | tcc | tgg | atc | cca | gag | ggc | gat | 624 |
| Val | Ala | Gly | Lys | Pro | Ala | Ala | Gln | Ile | Ser | Trp | Ile | Pro | Glu | Gly | Asp | |
| | | 195 | | | | | 200 | | | | | 205 | | | | |
| tgt | gcc | act | aag | caa | gaa | tac | tgg | agc | aat | ggc | aca | gtg | act | gtt | aag | 672 |
| Cys | Ala | Thr | Lys | Gln | Glu | Tyr | Trp | Ser | Asn | Gly | Thr | Val | Thr | Val | Lys | |
| | 210 | | | | | 215 | | | | | 220 | | | | | |
| agt | aca | tgc | cac | tgg | gag | gtc | cac | aat | gtg | tct | acc | gtg | acc | tgc | cac | 720 |
| Ser | Thr | Cys | His | Trp | Glu | Val | His | Asn | Val | Ser | Thr | Val | Thr | Cys | His | |
| 225 | | | | | 230 | | | | | 235 | | | | | 240 | |
| gtc | tcc | cat | ttg | act | ggc | aac | aag | agt | ctg | tac | ata | gag | cta | ctt | cct | 768 |
| Val | Ser | His | Leu | Thr | Gly | Asn | Lys | Ser | Leu | Tyr | Ile | Glu | Leu | Leu | Pro | |
| | | | | 245 | | | | | 250 | | | | | 255 | | |

```
gtt cca ggt gcc aaa aaa tca gca aaa tta tat att cca tat atc atc     816
Val Pro Gly Ala Lys Lys Ser Ala Lys Leu Tyr Ile Pro Tyr Ile Ile
        260                 265                 270 ctt act att att att ttg acc atc gtg gga ttc att tgg ttg ttg aaa     864
Leu Thr Ile Ile Ile Leu Thr Ile Val Gly Phe Ile Trp Leu Leu Lys
        275                 280                 285 gtc aat ggc tgc aga aaa tat aaa ttg aat aaa aca gaa tct act cca     912
Val Asn Gly Cys Arg Lys Tyr Lys Leu Asn Lys Thr Glu Ser Thr Pro
        290                 295                 300 gtt gtt gag gag gat gaa atg cag ccc tat gcc agc tac aca gag aag     960
Val Val Glu Glu Asp Glu Met Gln Pro Tyr Ala Ser Tyr Thr Glu Lys
305                 310                 315                 320 aac aat cct ctc tat gat act aca aac aag gtg aag gca tct cag gca    1008
Asn Asn Pro Leu Tyr Asp Thr Thr Asn Lys Val Lys Ala Ser Gln Ala
                325                 330                 335 tta caa agt gaa gtt gac aca gac ctc cat act tta taa                1047
Leu Gln Ser Glu Val Asp Thr Asp Leu His Thr Leu
                340                 345
```

<210> SEQ ID NO 2
<211> LENGTH: 348
<212> TYPE: PRT
<213> ORGANISM: Homo sapiens

<400> SEQUENCE: 2

```
Met Leu Cys Pro Trp Arg Thr Ala Asn Leu Gly Leu Leu Leu Ile Leu
1               5                   10                  15

Thr Ile Phe Leu Val Ala Glu Ala Glu Gly Ala Ala Gln Pro Asn Asn
            20                  25                  30

Ser Leu Met Leu Gln Thr Ser Lys Glu Asn His Ala Leu Ala Ser Ser
        35                  40                  45

Ser Leu Cys Met Asp Glu Lys Gln Ile Thr Gln Asn Tyr Ser Lys Val
    50                  55                  60

Leu Ala Glu Val Asn Thr Ser Trp Pro Val Lys Met Ala Thr Asn Ala
65                  70                  75                  80

Val Leu Cys Cys Pro Pro Ile Ala Leu Arg Asn Leu Ile Ile Ile Thr
                85                  90                  95

Trp Glu Ile Ile Leu Arg Gly Gln Pro Ser Cys Thr Lys Ala Tyr Arg
            100                 105                 110

Lys Glu Thr Asn Glu Thr Lys Glu Thr Asn Cys Thr Asp Glu Arg Ile
        115                 120                 125

Thr Trp Val Ser Arg Pro Asp Gln Asn Ser Asp Leu Gln Ile Arg Pro
    130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
                165                 170                 175

Glu Val Thr Leu Phe Gln Asn Arg Asn Arg Thr Ala Val Cys Lys Ala
            180                 185                 190

Val Ala Gly Lys Pro Ala Ala Gln Ile Ser Trp Ile Pro Glu Gly Asp
        195                 200                 205

Cys Ala Thr Lys Gln Glu Tyr Trp Ser Asn Gly Thr Val Thr Val Lys
    210                 215                 220

Ser Thr Cys His Trp Glu Val His Asn Val Ser Thr Val Thr Cys His
225                 230                 235                 240

Val Ser His Leu Thr Gly Asn Lys Ser Leu Tyr Ile Glu Leu Leu Pro
```

```
                        245                 250                 255
    Val Pro Gly Ala Lys Lys Ser Ala Lys Leu Tyr Ile Pro Tyr Ile Ile
                260                 265                 270

Leu Thr Ile Ile Ile Leu Thr Ile Val Gly Phe Ile Trp Leu Leu Lys
                275                 280                 285

Val Asn Gly Cys Arg Lys Tyr Lys Leu Asn Lys Thr Glu Ser Thr Pro
                290                 295                 300

Val Val Glu Glu Asp Glu Met Gln Pro Tyr Ala Ser Tyr Thr Glu Lys
    305                 310                 315                 320

Asn Asn Pro Leu Tyr Asp Thr Thr Asn Lys Val Lys Ala Ser Gln Ala
                325                 330                 335

Leu Gln Ser Glu Val Asp Thr Asp Leu His Thr Leu
                340                 345

<210> SEQ ID NO 3
<211> LENGTH: 981
<212> TYPE: DNA
<213> ORGANISM: Homo sapiens
<220> FEATURE:
<221> NAME/KEY: CDS
<222> LOCATION: (1)..(780)
<223> OTHER INFORMATION:

<400> SEQUENCE: 3 atg ctc tgc cct tgg aga act gct aac cta ggg cta ctg ttg att ttg      48
Met Leu Cys Pro Trp Arg Thr Ala Asn Leu Gly Leu Leu Leu Ile Leu
1               5                   10                  15 act atc ttc tta gtg gcc gaa gcg gag ggt gct gct caa cca aac aac      96
Thr Ile Phe Leu Val Ala Glu Ala Glu Gly Ala Ala Gln Pro Asn Asn
            20                  25                  30 tca tta atg ctg caa act agc aag gag aat cat gct tta gct tca agc     144
Ser Leu Met Leu Gln Thr Ser Lys Glu Asn His Ala Leu Ala Ser Ser
        35                  40                  45 agt tta tgt atg gat gaa aaa cag att aca cag aac tac tcg aaa gta     192
Ser Leu Cys Met Asp Glu Lys Gln Ile Thr Gln Asn Tyr Ser Lys Val
    50                  55                  60 ctc gca gaa gtt aac act tca tgg cct gta aag atg gct aca aat gct     240
Leu Ala Glu Val Asn Thr Ser Trp Pro Val Lys Met Ala Thr Asn Ala
65                  70                  75                  80 gtg ctt tgt tgc cct cct atc gca tta aga aat ttg atc ata ata aca     288
Val Leu Cys Cys Pro Pro Ile Ala Leu Arg Asn Leu Ile Ile Ile Thr
                85                  90                  95 tgg gaa ata atc ctg aga ggc cag cct tcc tgc aca aaa gcc tac agg     336
Trp Glu Ile Ile Leu Arg Gly Gln Pro Ser Cys Thr Lys Ala Tyr Arg
            100                 105                 110 aaa gaa aca aat gag acc aag gaa acc aac tgt act gat gag aga ata     384
Lys Glu Thr Asn Glu Thr Lys Glu Thr Asn Cys Thr Asp Glu Arg Ile
        115                 120                 125 acc tgg gtc tcc aga cct gat cag aat tcg gac ctt cag att cgt cca     432
Thr Trp Val Ser Arg Pro Asp Gln Asn Ser Asp Leu Gln Ile Arg Pro
    130                 135                 140 gtg gcc atc act cat gac ggg tat tac aga tgc ata atg gta aca cct     480
Val Ala Ile Thr His Asp Gly Tyr Tyr Arg Cys Ile Met Val Thr Pro
145                 150                 155                 160 gat ggg aat ttc cat cgt gga tat cac ctc caa gtg tta gtt aca cct     528
Asp Gly Asn Phe His Arg Gly Tyr His Leu Gln Val Leu Val Thr Pro
                165                 170                 175 gaa gtg acc ctg ttt caa aac agg aat aga act gca gta tgc aag gca     576
Glu Val Thr Leu Phe Gln Asn Arg Asn Arg Thr Ala Val Cys Lys Ala
            180                 185                 190
```

| | | | | | | | | | | | | | | | | |
|---|---|---|---|---|---|---|---|---|---|---|---|---|---|---|---|---|
| gtt | gca | ggg | aag | cca | gct | gcg | cag | atc | tcc | tgg | atc | cca | gag | ggc | gat | 624 |
| Val | Ala | Gly | Lys | Pro | Ala | Ala | Gln | Ile | Ser | Trp | Ile | Pro | Glu | Gly | Asp | |
| | | 195 | | | | | 200 | | | | | 205 | | | | |
| tgt | gcc | act | aag | caa | gaa | tac | tgg | agc | aat | ggc | aca | gtg | act | gtt | aag | 672 |
| Cys | Ala | Thr | Lys | Gln | Glu | Tyr | Trp | Ser | Asn | Gly | Thr | Val | Thr | Val | Lys | |
| 210 | | | | | 215 | | | | | 220 | | | | | | |
| agt | aca | tgc | cac | tgg | gag | gtc | cac | aat | gtg | tct | acc | gtg | acc | tgc | cac | 720 |
| Ser | Thr | Cys | His | Trp | Glu | Val | His | Asn | Val | Ser | Thr | Val | Thr | Cys | His | |
| 225 | | | | 230 | | | | | 235 | | | | | 240 | | |
| gtc | tcc | cat | ttg | act | ggc | aac | aag | agt | ctg | tac | ata | gag | cta | ctt | cct | 768 |
| Val | Ser | His | Leu | Thr | Gly | Asn | Lys | Ser | Leu | Tyr | Ile | Glu | Leu | Leu | Pro | |
| | | | 245 | | | | | 250 | | | | | 255 | | | |

| | | | | |
|---|---|---|---|---|
| gaa | aat | ata | aat tgaataaaac agaatctact ccagttgttg aggaggatga | 820 |
| Glu | Asn | Ile | Asn | |
| | | 260 | | | aatgcagccc tatgccagct acacagagaa gaacaatcct ctctatgata ctacaaacaa 880 ggtgaaggca tctcaggcat acaaagtga agttgacaca gacctccata ctttaaccgg 940 tgttctgact acaaggacga cgacgacaag tgagcggccg c 981

<210> SEQ ID NO 4
<211> LENGTH: 260
<212> TYPE: PRT
<213> ORGANISM: Homo sapiens

<400> SEQUENCE: 4

| | | | | | | | | | | | | | | |
|---|---|---|---|---|---|---|---|---|---|---|---|---|---|---|
| Met | Leu | Cys | Pro | Trp | Arg | Thr | Ala | Asn | Leu | Gly | Leu | Leu | Ile | Leu |
| 1 | | | | 5 | | | | | 10 | | | | | 15 |
| Thr | Ile | Phe | Leu | Val | Ala | Glu | Ala | Gly | Ala | Ala | Gln | Pro | Asn | Asn |
| | | | 20 | | | | | 25 | | | | | 30 | |
| Ser | Leu | Met | Leu | Gln | Thr | Ser | Lys | Glu | Asn | His | Ala | Leu | Ala | Ser | Ser |
| | | | 35 | | | | | 40 | | | | | 45 | | |
| Ser | Leu | Cys | Met | Asp | Glu | Lys | Gln | Ile | Thr | Gln | Asn | Tyr | Ser | Lys | Val |
| | 50 | | | | | 55 | | | | | 60 | | | | |
| Leu | Ala | Glu | Val | Asn | Thr | Ser | Trp | Pro | Val | Lys | Met | Ala | Thr | Asn | Ala |
| 65 | | | | | 70 | | | | | 75 | | | | | 80 |
| Val | Leu | Cys | Cys | Pro | Pro | Ile | Ala | Leu | Arg | Asn | Leu | Ile | Ile | Ile | Thr |
| | | | | 85 | | | | | 90 | | | | | 95 | |
| Trp | Glu | Ile | Ile | Leu | Arg | Gly | Gln | Pro | Ser | Cys | Thr | Lys | Ala | Tyr | Arg |
| | | | 100 | | | | | 105 | | | | | 110 | | |
| Lys | Glu | Thr | Asn | Glu | Thr | Lys | Glu | Thr | Asn | Cys | Thr | Asp | Glu | Arg | Ile |
| | | 115 | | | | | 120 | | | | | 125 | | | |
| Thr | Trp | Val | Ser | Arg | Pro | Asp | Gln | Asn | Ser | Asp | Leu | Gln | Ile | Arg | Pro |
| | 130 | | | | | 135 | | | | | 140 | | | | |
| Val | Ala | Ile | Thr | His | Asp | Gly | Tyr | Tyr | Arg | Cys | Ile | Met | Val | Thr | Pro |
| 145 | | | | | 150 | | | | | 155 | | | | | 160 |
| Asp | Gly | Asn | Phe | His | Arg | Gly | Tyr | His | Leu | Gln | Val | Leu | Val | Thr | Pro |
| | | | 165 | | | | | 170 | | | | | 175 | | |
| Glu | Val | Thr | Leu | Phe | Gln | Asn | Arg | Asn | Arg | Thr | Ala | Val | Cys | Lys | Ala |
| | | | 180 | | | | | 185 | | | | | 190 | | |
| Val | Ala | Gly | Lys | Pro | Ala | Ala | Gln | Ile | Ser | Trp | Ile | Pro | Glu | Gly | Asp |
| | | 195 | | | | | 200 | | | | | 205 | | | |
| Cys | Ala | Thr | Lys | Gln | Glu | Tyr | Trp | Ser | Asn | Gly | Thr | Val | Thr | Val | Lys |
| 210 | | | | | 215 | | | | | 220 | | | | | |
| Ser | Thr | Cys | His | Trp | Glu | Val | His | Asn | Val | Ser | Thr | Val | Thr | Cys | His |
| 225 | | | | 230 | | | | | 235 | | | | | 240 | |

```
                Val Ser His Leu Thr Gly Asn Lys Ser Leu Tyr Ile Glu Leu Leu Pro
                                245                 250                 255

Glu Asn Ile Asn
                            260

<210> SEQ ID NO 5
<211> LENGTH: 935
<212> TYPE: DNA
<213> ORGANISM: Homo sapiens
<220> FEATURE:
<221> NAME/KEY: CDS
<222> LOCATION: (1)..(771)
<223> OTHER INFORMATION:

<400> SEQUENCE: 5 atg ctc tgc cct tgg aga act gct aac cta ggg cta ctg ttg att ttg        48
Met Leu Cys Pro Trp Arg Thr Ala Asn Leu Gly Leu Leu Leu Ile Leu
1               5                   10                  15 act atc ttc tta gtg gcc gaa gcg gag ggt gct gct caa cca aac aac        96
Thr Ile Phe Leu Val Ala Glu Ala Glu Gly Ala Ala Gln Pro Asn Asn
                20                  25                  30 tca tta atg ctg caa act agc aag gag aat cat gct tta gct tca agc       144
Ser Leu Met Leu Gln Thr Ser Lys Glu Asn His Ala Leu Ala Ser Ser
            35                  40                  45 agt tta tgt atg gat gaa aaa cag att aca cag aac tac tcg aaa gta       192
Ser Leu Cys Met Asp Glu Lys Gln Ile Thr Gln Asn Tyr Ser Lys Val
        50                  55                  60 ctc gca gaa gtt aac act tca tgg cct gta aag atg gct aca aat gct       240
Leu Ala Glu Val Asn Thr Ser Trp Pro Val Lys Met Ala Thr Asn Ala
65                  70                  75                  80 gtg ctt tgt tgc cct cct atc gca tta aga aat ttg atc ata ata aca       288
Val Leu Cys Cys Pro Pro Ile Ala Leu Arg Asn Leu Ile Ile Ile Thr
                85                  90                  95 tgg gaa ata atc ctg aga ggc cag cct tcc tgc aca aaa gcc tac agg       336
Trp Glu Ile Ile Leu Arg Gly Gln Pro Ser Cys Thr Lys Ala Tyr Arg
                100                 105                 110 aaa gaa aca aat gag acc aag gaa acc aac tgt act gat gag aga ata       384
Lys Glu Thr Asn Glu Thr Lys Glu Thr Asn Cys Thr Asp Glu Arg Ile
            115                 120                 125 acc tgg gtc tcc aga cct gat cag aat tcg gac ctt cag att cgt cca       432
Thr Trp Val Ser Arg Pro Asp Gln Asn Ser Asp Leu Gln Ile Arg Pro
        130                 135                 140 gtg gcc atc act cat gac ggg tat tac aga tgc ata atg gta aca cct       480
Val Ala Ile Thr His Asp Gly Tyr Tyr Arg Cys Ile Met Val Thr Pro
145                 150                 155                 160 gat ggg aat ttc cat cgt gga tat cac ctc caa gtg tta gtt aca cct       528
Asp Gly Asn Phe His Arg Gly Tyr His Leu Gln Val Leu Val Thr Pro
                165                 170                 175 gaa gtg acc ctg ttt caa aac agg aat aga act gca gta tgc aag gca       576
Glu Val Thr Leu Phe Gln Asn Arg Asn Arg Thr Ala Val Cys Lys Ala
                180                 185                 190 gtt gca ggg aag cca gct gcg cag atc tcc tgg atc cca gag ggc gat       624
Val Ala Gly Lys Pro Ala Ala Gln Ile Ser Trp Ile Pro Glu Gly Asp
            195                 200                 205 tgt gcc act aag caa gaa tac tgg agc aat ggc aca gtg act gtt aag       672
Cys Ala Thr Lys Gln Glu Tyr Trp Ser Asn Gly Thr Val Thr Val Lys
        210                 215                 220 agt aca tgc cac tgg gag gtc cac aat gtg tct acc gtg acc tgc cac       720
Ser Thr Cys His Trp Glu Val His Asn Val Ser Thr Val Thr Cys His
225                 230                 235                 240
```

-continued

```
gtc tcc cat ttg act ggc aac aag agt ctg tac ata gag cta ctt cct    768
Val Ser His Leu Thr Gly Asn Lys Ser Leu Tyr Ile Glu Leu Leu Pro
                245                 250                 255 gga tgaaatgcag ccctatgcca gctacacaga gaagaacaat cctctctatg         821
Gly atactacaaa caaggtgaag gcatctcagg cattacaaag tgaagttgac acagacctcc  881
atactttaac cggtgttctg actacaagga cgacgacgac aagtgagcgg ccgc        935
```

<210> SEQ ID NO 6
<211> LENGTH: 257
<212> TYPE: PRT
<213> ORGANISM: Homo sapiens

<400> SEQUENCE: 6

```
Met Leu Cys Pro Trp Arg Thr Ala Asn Leu Gly Leu Leu Ile Leu
1               5                   10                  15

Thr Ile Phe Leu Val Ala Glu Ala Glu Gly Ala Ala Gln Pro Asn Asn
                20                  25                  30

Ser Leu Met Leu Gln Thr Ser Lys Glu Asn His Ala Leu Ala Ser Ser
            35                  40                  45

Ser Leu Cys Met Asp Glu Lys Gln Ile Thr Gln Asn Tyr Ser Lys Val
        50                  55                  60

Leu Ala Glu Val Asn Thr Ser Trp Pro Val Lys Met Ala Thr Asn Ala
65                  70                  75                  80

Val Leu Cys Cys Pro Pro Ile Ala Leu Arg Asn Leu Ile Ile Ile Thr
                85                  90                  95

Trp Glu Ile Ile Leu Arg Gly Gln Pro Ser Cys Thr Lys Ala Tyr Arg
                100                 105                 110

Lys Glu Thr Asn Glu Thr Lys Glu Thr Asn Cys Thr Asp Glu Arg Ile
            115                 120                 125

Thr Trp Val Ser Arg Pro Asp Gln Asn Ser Asp Leu Gln Ile Arg Pro
        130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
                165                 170                 175

Glu Val Thr Leu Phe Gln Asn Arg Asn Arg Thr Ala Val Cys Lys Ala
                180                 185                 190

Val Ala Gly Lys Pro Ala Ala Gln Ile Ser Trp Ile Pro Glu Gly Asp
            195                 200                 205

Cys Ala Thr Lys Gln Glu Tyr Trp Ser Asn Gly Thr Val Thr Val Lys
        210                 215                 220

Ser Thr Cys His Trp Glu Val His Asn Val Ser Thr Val Thr Cys His
225                 230                 235                 240

Val Ser His Leu Thr Gly Asn Lys Ser Leu Tyr Ile Glu Leu Leu Pro
                245                 250                 255

Gly
```

<210> SEQ ID NO 7
<211> LENGTH: 981
<212> TYPE: DNA
<213> ORGANISM: Mus sp.
<220> FEATURE:
<221> NAME/KEY: CDS
<222> LOCATION: (1)..(981)
<223> OTHER INFORMATION:

-continued

<400> SEQUENCE: 7

| | | | | | | | | | | | | | | | | |
|---|---|---|---|---|---|---|---|---|---|---|---|---|---|---|---|---|
| atg | ttt | tgc | ttt | tgg | aga | act | tct | gcc | cta | gca | gtg | ctc | tta | ata | tgg | 48 |
| Met | Phe | Cys | Phe | Trp | Arg | Thr | Ser | Ala | Leu | Ala | Val | Leu | Leu | Ile | Trp | |
| 1 | | | | 5 | | | | | 10 | | | | | 15 | | |
| ggg | gtc | ttt | gtg | gct | ggg | tca | agt | tgt | act | gat | aag | aat | caa | aca | aca | 96 |
| Gly | Val | Phe | Val | Ala | Gly | Ser | Ser | Cys | Thr | Asp | Lys | Asn | Gln | Thr | Thr | |
| | | | 20 | | | | | 25 | | | | | 30 | | | |
| cag | aac | aac | agt | tca | tct | cct | ctg | aca | caa | gtg | aac | act | aca | gtg | tct | 144 |
| Gln | Asn | Asn | Ser | Ser | Ser | Pro | Leu | Thr | Gln | Val | Asn | Thr | Thr | Val | Ser | |
| | | 35 | | | | | 40 | | | | | 45 | | | | |
| gta | cag | ata | ggt | aca | aag | gct | ctg | ctc | tgc | tgc | ttt | tct | att | cca | ctg | 192 |
| Val | Gln | Ile | Gly | Thr | Lys | Ala | Leu | Leu | Cys | Cys | Phe | Ser | Ile | Pro | Leu | |
| | 50 | | | | | 55 | | | | | 60 | | | | | |
| aca | aaa | gca | gta | tta | atc | aca | tgg | ata | ata | aag | ctc | aga | ggc | ctg | cca | 240 |
| Thr | Lys | Ala | Val | Leu | Ile | Thr | Trp | Ile | Ile | Lys | Leu | Arg | Gly | Leu | Pro | |
| 65 | | | | 70 | | | | | 75 | | | | | 80 | | |
| tcc | tgc | aca | ata | gca | tac | aaa | gta | gat | aca | aag | acc | aat | gaa | acc | agc | 288 |
| Ser | Cys | Thr | Ile | Ala | Tyr | Lys | Val | Asp | Thr | Lys | Thr | Asn | Glu | Thr | Ser | |
| | | | 85 | | | | | 90 | | | | | 95 | | | |
| tgc | ttg | ggc | agg | aac | atc | acc | tgg | gcc | tcc | aca | cct | gac | cac | agt | cct | 336 |
| Cys | Leu | Gly | Arg | Asn | Ile | Thr | Trp | Ala | Ser | Thr | Pro | Asp | His | Ser | Pro | |
| | | 100 | | | | | 105 | | | | | 110 | | | | |
| gaa | ctt | cag | atc | agt | gca | gtg | acc | ctc | cag | cat | gag | ggg | act | tac | aca | 384 |
| Glu | Leu | Gln | Ile | Ser | Ala | Val | Thr | Leu | Gln | His | Glu | Gly | Thr | Tyr | Thr | |
| | 115 | | | | | 120 | | | | | 125 | | | | | |
| tgt | gag | aca | gta | aca | cct | gaa | ggg | aat | ttt | gaa | aaa | aac | tat | gac | ctc | 432 |
| Cys | Glu | Thr | Val | Thr | Pro | Glu | Gly | Asn | Phe | Glu | Lys | Asn | Tyr | Asp | Leu | |
| 130 | | | | 135 | | | | | 140 | | | | | | | |
| caa | gtg | ctg | gtg | ccc | cct | gaa | gta | acc | tac | ttt | cca | gag | aaa | aac | aga | 480 |
| Gln | Val | Leu | Val | Pro | Pro | Glu | Val | Thr | Tyr | Phe | Pro | Glu | Lys | Asn | Arg | |
| 145 | | | | 150 | | | | | 155 | | | | | 160 | | |
| tct | gca | gtc | tgt | gag | gca | atg | gca | ggc | aag | cct | gct | gca | cag | atc | tct | 528 |
| Ser | Ala | Val | Cys | Glu | Ala | Met | Ala | Gly | Lys | Pro | Ala | Ala | Gln | Ile | Ser | |
| | | | 165 | | | | | 170 | | | | | 175 | | | |
| tgg | tct | cca | gat | ggg | gac | tgt | gtc | act | acg | agt | gaa | tca | cac | agc | aat | 576 |
| Trp | Ser | Pro | Asp | Gly | Asp | Cys | Val | Thr | Thr | Ser | Glu | Ser | His | Ser | Asn | |
| | | 180 | | | | | 185 | | | | | 190 | | | | |
| ggc | act | gtg | act | gtc | agg | agc | aca | tgc | cac | tgg | gag | cag | aac | aat | gtg | 624 |
| Gly | Thr | Val | Thr | Val | Arg | Ser | Thr | Cys | His | Trp | Glu | Gln | Asn | Asn | Val | |
| | 195 | | | | | 200 | | | | | 205 | | | | | |
| tct | gat | gtg | tcc | tgc | att | gtc | tct | cat | ttg | act | ggt | aac | caa | tct | ctg | 672 |
| Ser | Asp | Val | Ser | Cys | Ile | Val | Ser | His | Leu | Thr | Gly | Asn | Gln | Ser | Leu | |
| 210 | | | | 215 | | | | | 220 | | | | | | | |
| tcc | ata | gaa | ctg | agt | aga | ggt | ggt | aac | caa | tca | tta | cga | cca | tat | att | 720 |
| Ser | Ile | Glu | Leu | Ser | Arg | Gly | Gly | Asn | Gln | Ser | Leu | Arg | Pro | Tyr | Ile | |
| 225 | | | | 230 | | | | | 235 | | | | | 240 | | |
| cca | tac | atc | ata | cca | tca | att | atc | att | ttg | atc | atc | ata | gga | tgc | att | 768 |
| Pro | Tyr | Ile | Ile | Pro | Ser | Ile | Ile | Ile | Leu | Ile | Ile | Ile | Gly | Cys | Ile | |
| | | | 245 | | | | | 250 | | | | | 255 | | | |
| tgt | ctt | ttg | aaa | atc | agt | ggc | ttc | aga | aaa | tgc | aaa | ttg | cca | aaa | tta | 816 |
| Cys | Leu | Leu | Lys | Ile | Ser | Gly | Phe | Arg | Lys | Cys | Lys | Leu | Pro | Lys | Leu | |
| | | 260 | | | | | 265 | | | | | 270 | | | | |
| gaa | gct | act | tca | gct | att | gag | gag | gat | gaa | atg | cag | cct | tat | gct | agc | 864 |
| Glu | Ala | Thr | Ser | Ala | Ile | Glu | Glu | Asp | Glu | Met | Gln | Pro | Tyr | Ala | Ser | |
| | 275 | | | | | 280 | | | | | 285 | | | | | |
| tat | aca | gag | aag | agc | aat | cca | ctc | tat | gat | act | gtg | act | aag | gtg | gag | 912 |
| Tyr | Thr | Glu | Lys | Ser | Asn | Pro | Leu | Tyr | Asp | Thr | Val | Thr | Lys | Val | Glu | |
| 290 | | | | 295 | | | | | 300 | | | | | | | |
| gca | ttt | cca | gta | tca | caa | ggc | gaa | gtc | aat | ggc | aca | gac | tgc | ctt | act | 960 |

```
Ala Phe Pro Val Ser Gln Gly Glu Val Asn Gly Thr Asp Cys Leu Thr
305                 310                 315                 320 ttg tcg gcc att gga atc tag                                       981
Leu Ser Ala Ile Gly Ile
                325

<210> SEQ ID NO 8
<211> LENGTH: 326
<212> TYPE: PRT
<213> ORGANISM: Mus sp.

<400> SEQUENCE: 8

Met Phe Cys Phe Trp Arg Thr Ser Ala Leu Ala Val Leu Leu Ile Trp
1               5                   10                  15

Gly Val Phe Val Ala Gly Ser Ser Cys Thr Asp Lys Asn Gln Thr Thr
            20                  25                  30

Gln Asn Asn Ser Ser Ser Pro Leu Thr Gln Val Asn Thr Thr Val Ser
                35                  40                  45

Val Gln Ile Gly Thr Lys Ala Leu Leu Cys Cys Phe Ser Ile Pro Leu
    50                  55                  60

Thr Lys Ala Val Leu Ile Thr Trp Ile Ile Lys Leu Arg Gly Leu Pro
65                  70                  75                  80

Ser Cys Thr Ile Ala Tyr Lys Val Asp Thr Lys Thr Asn Glu Thr Ser
                85                  90                  95

Cys Leu Gly Arg Asn Ile Thr Trp Ala Ser Thr Pro Asp His Ser Pro
            100                 105                 110

Glu Leu Gln Ile Ser Ala Val Thr Leu Gln His Glu Gly Thr Tyr Thr
        115                 120                 125

Cys Glu Thr Val Thr Pro Glu Gly Asn Phe Glu Lys Asn Tyr Asp Leu
    130                 135                 140

Gln Val Leu Val Pro Pro Glu Val Thr Tyr Phe Pro Glu Lys Asn Arg
145                 150                 155                 160

Ser Ala Val Cys Glu Ala Met Ala Gly Lys Pro Ala Ala Gln Ile Ser
                165                 170                 175

Trp Ser Pro Asp Gly Asp Cys Val Thr Thr Ser Glu Ser His Ser Asn
            180                 185                 190

Gly Thr Val Thr Val Arg Ser Thr Cys His Trp Glu Gln Asn Asn Val
        195                 200                 205

Ser Asp Val Ser Cys Ile Val Ser His Leu Thr Gly Asn Gln Ser Leu
    210                 215                 220

Ser Ile Glu Leu Ser Arg Gly Gly Asn Gln Ser Leu Arg Pro Tyr Ile
225                 230                 235                 240

Pro Tyr Ile Ile Pro Ser Ile Ile Leu Ile Ile Gly Cys Ile
                245                 250                 255

Cys Leu Leu Lys Ile Ser Gly Phe Arg Lys Cys Lys Leu Pro Lys Leu
            260                 265                 270

Glu Ala Thr Ser Ala Ile Glu Glu Asp Glu Met Gln Pro Tyr Ala Ser
        275                 280                 285

Tyr Thr Glu Lys Ser Asn Pro Leu Tyr Asp Thr Thr Lys Val Glu
    290                 295                 300

Ala Phe Pro Val Ser Gln Gly Glu Val Asn Gly Thr Asp Cys Leu Thr
305                 310                 315                 320

Leu Ser Ala Ile Gly Ile
                325
```

-continued

```
<210> SEQ ID NO 9
<211> LENGTH: 666
<212> TYPE: DNA
<213> ORGANISM: Mus sp.
<220> FEATURE:
<221> NAME/KEY: CDS
<222> LOCATION: (1)..(666)
<223> OTHER INFORMATION:

<400> SEQUENCE: 9 atg ttt tgc ttt tgg aga act tct gcc cta gca gtg ctc tta ata tgg      48
Met Phe Cys Phe Trp Arg Thr Ser Ala Leu Ala Val Leu Leu Ile Trp
1               5                   10                  15 ggg gtc ttt gtg gct ggg tca agt tgt act gat aag aat caa aca aca      96
Gly Val Phe Val Ala Gly Ser Ser Cys Thr Asp Lys Asn Gln Thr Thr
            20                  25                  30 cag aac aac agt tca tct cct ctg aca caa gtg ccc cct gaa gta acc     144
Gln Asn Asn Ser Ser Ser Pro Leu Thr Gln Val Pro Pro Glu Val Thr
        35                  40                  45 tac ttt cca gag aaa aac aga tct gca gtc tgt gag gca atg gca ggc     192
Tyr Phe Pro Glu Lys Asn Arg Ser Ala Val Cys Glu Ala Met Ala Gly
    50                  55                  60 aag cct gct gca cag atc tct tgg tct cca gat ggg gac tgt gtc act     240
Lys Pro Ala Ala Gln Ile Ser Trp Ser Pro Asp Gly Asp Cys Val Thr
65                  70                  75                  80 acg agt gaa tca cac agc aat ggc act gtg act gtc agg agc aca tgc     288
Thr Ser Glu Ser His Ser Asn Gly Thr Val Thr Val Arg Ser Thr Cys
                85                  90                  95 cac tgg gag cag aac aat gtg tct gat gtg tcc tgc att gtc tct cat     336
His Trp Glu Gln Asn Asn Val Ser Asp Val Ser Cys Ile Val Ser His
            100                 105                 110 ttg act ggt aac caa tct ctg tcc ata gaa ctg agt aga ggt ggt aac     384
Leu Thr Gly Asn Gln Ser Leu Ser Ile Glu Leu Ser Arg Gly Gly Asn
        115                 120                 125 caa tca tta cga cca tat att cca tac atc ata cca tca att atc att     432
Gln Ser Leu Arg Pro Tyr Ile Pro Tyr Ile Ile Pro Ser Ile Ile Ile
    130                 135                 140 ttg atc atc ata gga tgc att tgt ctt ttg aaa atc agt ggc ttc aga     480
Leu Ile Ile Ile Gly Cys Ile Cys Leu Leu Lys Ile Ser Gly Phe Arg
145                 150                 155                 160 aaa tgc aaa ttg cca aaa tta gaa gct act tca gct att gag gag gat     528
Lys Cys Lys Leu Pro Lys Leu Glu Ala Thr Ser Ala Ile Glu Glu Asp
                165                 170                 175 gaa atg cag cct tat gct agc tat aca gag aag agc aat cca ctc tat     576
Glu Met Gln Pro Tyr Ala Ser Tyr Thr Glu Lys Ser Asn Pro Leu Tyr
            180                 185                 190 gat act gtg act aag gtg gag gca ttt cca gta tca caa ggc gaa gtc     624
Asp Thr Val Thr Lys Val Glu Ala Phe Pro Val Ser Gln Gly Glu Val
        195                 200                 205 aat ggc aca gac tgc ctt act ttg tcg gcc att gga atc tag             666
Asn Gly Thr Asp Cys Leu Thr Leu Ser Ala Ile Gly Ile
    210                 215                 220

<210> SEQ ID NO 10
<211> LENGTH: 221
<212> TYPE: PRT
<213> ORGANISM: Mus sp.

<400> SEQUENCE: 10

Met Phe Cys Phe Trp Arg Thr Ser Ala Leu Ala Val Leu Leu Ile Trp
1               5                   10                  15

Gly Val Phe Val Ala Gly Ser Ser Cys Thr Asp Lys Asn Gln Thr Thr
```

-continued

```
                20                  25                  30
Gln Asn Asn Ser Ser Ser Pro Leu Thr Gln Val Pro Glu Val Thr
             35                  40                  45

Tyr Phe Pro Glu Lys Asn Arg Ser Ala Val Cys Glu Ala Met Ala Gly
 50                  55                  60

Lys Pro Ala Ala Gln Ile Ser Trp Ser Pro Asp Gly Asp Cys Val Thr
 65                  70                  75                  80

Thr Ser Glu Ser His Ser Asn Gly Thr Val Thr Val Arg Ser Thr Cys
                 85                  90                  95

His Trp Glu Gln Asn Asn Val Ser Asp Val Ser Cys Ile Val Ser His
            100                 105                 110

Leu Thr Gly Asn Gln Ser Leu Ser Ile Glu Leu Ser Arg Gly Gly Asn
        115                 120                 125

Gln Ser Leu Arg Pro Tyr Ile Pro Tyr Ile Ile Pro Ser Ile Ile Ile
    130                 135                 140

Leu Ile Ile Ile Gly Cys Ile Cys Leu Leu Lys Ile Ser Gly Phe Arg
145                 150                 155                 160

Lys Cys Lys Leu Pro Lys Leu Glu Ala Thr Ser Ala Ile Glu Glu Asp
                165                 170                 175

Glu Met Gln Pro Tyr Ala Ser Tyr Thr Glu Lys Ser Asn Pro Leu Tyr
            180                 185                 190

Asp Thr Val Thr Lys Val Glu Ala Phe Pro Val Ser Gln Gly Glu Val
        195                 200                 205

Asn Gly Thr Asp Cys Leu Thr Leu Ser Ala Ile Gly Ile
    210                 215                 220
```

<210> SEQ ID NO 11
<211> LENGTH: 881
<212> TYPE: DNA
<213> ORGANISM: Mus sp.
<220> FEATURE:
<221> NAME/KEY: CDS
<222> LOCATION: (1)..(714)
<223> OTHER INFORMATION:

<400> SEQUENCE: 11

```
atg ttt tgc ttt tgg aga act tct gcc cta gca gtg ctc tta ata tgg      48
Met Phe Cys Phe Trp Arg Thr Ser Ala Leu Ala Val Leu Leu Ile Trp
 1               5                  10                  15 ggg gtc ttt gtg gct ggg tca agt tgt act gat aag aat caa aca aca      96
Gly Val Phe Val Ala Gly Ser Ser Cys Thr Asp Lys Asn Gln Thr Thr
             20                  25                  30 cag aac aac agt tca tct cct ctg aca caa gtg aac act aca gtg tct     144
Gln Asn Asn Ser Ser Ser Pro Leu Thr Gln Val Asn Thr Thr Val Ser
         35                  40                  45 gta cag ata ggt aca aag gct ctg ctc tgc tgc ttt tct att cca ctg     192
Val Gln Ile Gly Thr Lys Ala Leu Leu Cys Cys Phe Ser Ile Pro Leu
 50                  55                  60 aca aaa gca gta tta atc aca tgg ata ata aag ctc aga ggc ctg cca     240
Thr Lys Ala Val Leu Ile Thr Trp Ile Ile Lys Leu Arg Gly Leu Pro
 65                  70                  75                  80 tcc tgc aca ata gca tac aaa gta gat aca aag acc aat gaa acc agc     288
Ser Cys Thr Ile Ala Tyr Lys Val Asp Thr Lys Thr Asn Glu Thr Ser
                 85                  90                  95 tgc ttg ggc agg aac atc acc tgg gcc tcc aca cct gac cac agt cct     336
Cys Leu Gly Arg Asn Ile Thr Trp Ala Ser Thr Pro Asp His Ser Pro
            100                 105                 110 gaa ctt cag atc agt gca gtg acc ctc cag cat gag ggg act tac aca     384
```

-continued

```
Glu Leu Gln Ile Ser Ala Val Thr Leu Gln His Glu Gly Thr Tyr Thr
        115                 120                 125 tgt gag aca gta aca cct gaa ggg aat ttt gaa aaa aac tat gac ctc     432
Cys Glu Thr Val Thr Pro Glu Gly Asn Phe Glu Lys Asn Tyr Asp Leu
    130                 135                 140 caa gtg ctg gtg ccc cct gaa gta acc tac ttt cca gag aaa aac aga    480
Gln Val Leu Val Pro Pro Glu Val Thr Tyr Phe Pro Glu Lys Asn Arg
145                 150                 155                 160 tct gca gtc tgt gag gca atg gca ggc aag cct gct gca cag atc tct    528
Ser Ala Val Cys Glu Ala Met Ala Gly Lys Pro Ala Ala Gln Ile Ser
                165                 170                 175 tgg tct cca gat ggg gac tgt gtc act acg agt gaa tca cac agc aat    576
Trp Ser Pro Asp Gly Asp Cys Val Thr Thr Ser Glu Ser His Ser Asn
            180                 185                 190 ggc act gtg act gtc agg agc aca tgc cac tgg gag cag aac aat gtg    624
Gly Thr Val Thr Val Arg Ser Thr Cys His Trp Glu Gln Asn Asn Val
        195                 200                 205 tct gat gtg tcc tgc att gtc tct cat ttg act ggt aac caa tct ctg    672
Ser Asp Val Ser Cys Ile Val Ser His Leu Thr Gly Asn Gln Ser Leu
    210                 215                 220 tcc ata gaa ctg agt aga ggt gaa aat gca aat tgc caa aat            714
Ser Ile Glu Leu Ser Arg Gly Glu Asn Ala Asn Cys Gln Asn
225                 230                 235 tagaagctac ttcagctatt gaggaggatg aaatgcagcc ttatgctagc tatacagaga  774
agagcaatcc actctatgat actgtgacta aggtggaggc atttccagta tcacaaggcg  834
aagtcaatgg cacagactgc cttactttgt cggccattgg aatctag                881

<210> SEQ ID NO 12
<211> LENGTH: 238
<212> TYPE: PRT
<213> ORGANISM: Mus sp.

<400> SEQUENCE: 12

Met Phe Cys Phe Trp Arg Thr Ser Ala Leu Ala Val Leu Leu Ile Trp
1               5                   10                  15

Gly Val Phe Val Ala Gly Ser Ser Cys Thr Asp Lys Asn Gln Thr Thr
            20                  25                  30

Gln Asn Asn Ser Ser Ser Pro Leu Thr Gln Val Asn Thr Thr Val Ser
        35                  40                  45

Val Gln Ile Gly Thr Lys Ala Leu Leu Cys Cys Phe Ser Ile Pro Leu
    50                  55                  60

Thr Lys Ala Val Leu Ile Thr Trp Ile Ile Lys Leu Arg Gly Leu Pro
65                  70                  75                  80

Ser Cys Thr Ile Ala Tyr Lys Val Asp Thr Lys Thr Asn Glu Thr Ser
                85                  90                  95

Cys Leu Gly Arg Asn Ile Thr Trp Ala Ser Thr Pro Asp His Ser Pro
            100                 105                 110

Glu Leu Gln Ile Ser Ala Val Thr Leu Gln His Glu Gly Thr Tyr Thr
        115                 120                 125

Cys Glu Thr Val Thr Pro Glu Gly Asn Phe Glu Lys Asn Tyr Asp Leu
    130                 135                 140

Gln Val Leu Val Pro Pro Glu Val Thr Tyr Phe Pro Glu Lys Asn Arg
145                 150                 155                 160

Ser Ala Val Cys Glu Ala Met Ala Gly Lys Pro Ala Ala Gln Ile Ser
                165                 170                 175

Trp Ser Pro Asp Gly Asp Cys Val Thr Thr Ser Glu Ser His Ser Asn
```

```
                    180                 185                 190
Gly Thr Val Thr Val Arg Ser Thr Cys His Trp Glu Gln Asn Asn Val
        195                 200                 205

Ser Asp Val Ser Cys Ile Val Ser His Leu Thr Gly Asn Gln Ser Leu
    210                 215                 220

Ser Ile Glu Leu Ser Arg Gly Glu Asn Ala Asn Cys Gln Asn
225                 230                 235
```